US011745004B1

(12) United States Patent
Beltrán Calva et al.

(10) Patent No.: US 11,745,004 B1
(45) Date of Patent: Sep. 5, 2023

(54) VENTRICULAR ASSIST DEVICES AND METHODS

(71) Applicant: VITALMEX INTERNACIONAL S.A. DE C.V., Municipio Tlalnepantla (MX)

(72) Inventors: Adrian Beltrán Calva, Municipio Tlalnepantla (MX); Cynthia Denisse Anaya Romo, Municipio Tlalnepantla (MX); Jesús Salvador Carlos Robles, Municipio Tlalnepantla (MX)

(73) Assignee: VITALMEX INTERNACIONAL S.A. DE C.V., Municipio Tlalnepantla (MX)

( * ) Notice: Subject to any disclaimer, the term of this patent is extended or adjusted under 35 U.S.C. 154(b) by 0 days.

(21) Appl. No.: 17/865,940

(22) Filed: Jul. 15, 2022

(51) Int. Cl.
*A61M 60/178* (2021.01)
*A61M 60/427* (2021.01)
*A61M 60/268* (2021.01)
*A61M 60/894* (2021.01)

(52) U.S. Cl.
CPC ........ *A61M 60/178* (2021.01); *A61M 60/268* (2021.01); *A61M 60/427* (2021.01); *A61M 60/894* (2021.01)

(58) Field of Classification Search
None
See application file for complete search history.

(56) References Cited

U.S. PATENT DOCUMENTS

| 5,980,448 | A | * | 11/1999 | Heilman | A61M 60/876 600/16 |
| 2004/0249254 | A1 | * | 12/2004 | Racchini | A61B 5/150175 600/347 |
| 2022/0296878 | A1 | * | 9/2022 | Tsui | A61M 60/835 |

* cited by examiner

*Primary Examiner* — Catherine M Voorhees
*Assistant Examiner* — Elizabeth K So

(57) ABSTRACT

Embodiments include Ventricular Assist Devices (VADs) with clips that help hold a cannula to the VAD. In some embodiments the clip embraces a cannula that has been placed around a cannula connector. In further embodiments an additional clip connects the first clip to the VAD housing preventing the first clip from slipping. The clip and additional clip may form a single piece. Further embodiments include a blood pumping sac located inside a cavity in the VAD forming one or more air chambers between the sac and the cavity walls, and an airflow channel leading from the air chambers to an airflow port allowing the sac to be evenly pressurized and depressurized. Still further embodiments include one or more purge devices that assist in removing bubbles from the VAD and helping connect cannulas to the VAD. Additional embodiments include a torqueable wrench to facilitate use and proper sealing of the device.

14 Claims, 15 Drawing Sheets

US 11,745,004 B1

VENTRICULAR ASSIST DEVICES AND METHODS

FIELD

Embodiments of this disclosure relate generally to medical devices, and more specifically to ventricular assist devices ("VADs").

BACKGROUND

A ventricular assist device ("VAD") is used to help supplement the hearts pumping action, such as during and after certain kinds of surgery and in situations where a complete cardiopulmonary bypass, such as using a heart-lung machine, is neither needed nor advisable in light of the serious side effects associated therewith. The ventricular assist device typically utilizes a pair of cannulas (for example, tubing) and some sort of pump operably connected to the cannulas. In use, the cannulas are attached to either the left side of the heart (in which case the device is commonly referred to as a left ventricular assist device, LVAD) or to the right side of the heart (in which case the device is commonly referred to as a right ventricular assist device, RVAD) "in parallel" with the heart with the pump supplementing the heart's pumping action, but not completely bypassing it. Alternatively, a pump may be directly implanted into the body.

BRIEF SUMMARY

It was realized by the inventors of the present disclosure that problems exist with certain forms of VADs, including the manner in which cannulas connect to the VADs, and that improvements are needed. For example, in some VAD designs the cannulas connected to the ventricular assist device do not firmly affix to the ventricular assist device allowing axial and/or lateral (for example, crosswise) movement of the cannulas. Even in VADs utilizing some type of cannula holder, the cannula holder was difficult to install and could not be utilized after the cannula was already connected to the ventricular assist device, which in some VADs was due to the ventricular assist device's closed design. In addition, air pumped into the ventricular assist device when pressurizing or depressurizing the pump's sac was not consistently and homogeneously distributed to the sac. Furthermore, the pump housing was sometimes damaged because the fastener connecting the cannula to the pump housing exerted excessive force on the pump housing in order to prevent air from coming into or out from the pump housing. Still further, in many designs it was difficult to remove bubbles from the sac before implanting the cannulas. Consequently, the inventors realized there is a need for an improved fastening cannula for a ventricular access device, including those with optional connectors and cannula holders.

Certain preferred features of the present invention address these and other needs and provide other important advantages.

This as well as other embodiments, aspects, advantages and alternatives will become apparent to those of ordinary skill in the art by reading the following detailed description, with reference where appropriate to the accompanying drawings. Further, it should be understood that this summary and other descriptions and figures provided herein are intended to illustrate embodiments by way of example only and, as such, that numerous variations are possible. For example, combined, distributed, eliminated, or otherwise changed, while remaining within the scope of the embodiments as claimed.

BRIEF DESCRIPTION OF THE DRAWINGS

Some of the figures shown herein may include dimensions or may have been created from scaled drawings. However, such dimensions, or the relative scaling within a figure, are by way of example, and not to be construed as limiting

DETAILED DESCRIPTION OF THE ILLUSTRATED EMBODIMENTS

Figure 1:
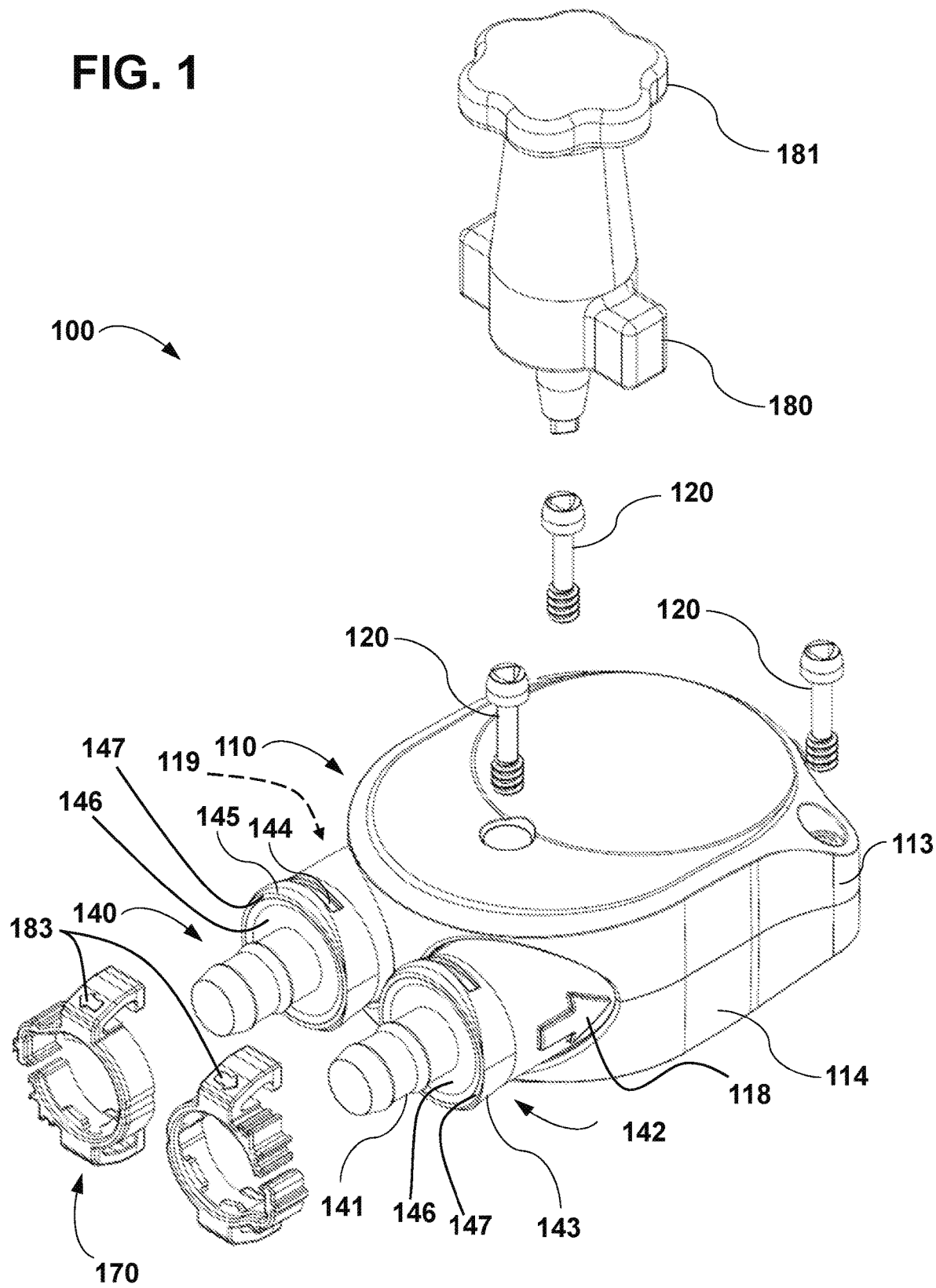
FIG. 1 is a perspective view of a ventricular assist device according to one embodiment of the present disclosure.

Reference will now be made in detail to embodiments, examples of which are illustrated in the accompanying drawings. The terminology used in the description herein is for the purpose of describing particular embodiments only and is not intended to be limiting. Any embodiment or feature described herein as being an "example" or "exemplary" is not necessarily to be construed as preferred or advantageous over other embodiments or features. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Any reference to "invention" or "embodiment" within this document is a reference to an embodiment of a family of inventions, with no single embodiment including features that are necessarily included in all embodiments, unless otherwise stated. Furthermore, although there may be references to benefits or advantages provided by some embodiments, other embodiments may not include those same benefits or advantages, or may include different benefits or advantages. Any benefits or advantages described herein are not to be construed as limiting to any of the claims.

Specific quantities (spatial dimensions, temperatures, pressures, times, force, resistance, current, voltage, concentrations, wavelengths, frequencies, heat transfer coefficients, dimensionless parameters, etc.) may be used explicitly or implicitly herein, such specific quantities are presented as examples only and are approximate values unless otherwise indicated. Discussions pertaining to specific compositions of matter, if present, are presented as examples only and do not limit the applicability of other compositions of matter, especially other compositions of matter with similar properties, unless otherwise indicated.

An example embodiment of the present disclosure is directed to a ventricular assist device (VAD) that connects to at least one cannula for assisting in pumping blood to and from a heart. The VAD includes a pump housing defining an interior chamber with a pump inlet and a pump outlet, a cannula connector attached to the pump inlet for connecting the pump housing to a cannula, a cannula connector connected the pump outlet for connecting the pump housing to a cannula, a sac disposed in the interior chamber and connected to the pump inlet and the pump outlet, an airflow channel disposed at an end of the pump housing for flowing air from or to the interior chamber to pressurize or depressurize the sac, and a cannula holder configured to fasten the cannula to the connector. Each of the cannula connectors can include a protruding cannula connector that is inserted into the cannula and a pump housing connector connected to the pump housing. Either before or after a cannula is attached to a cannula connector, a cannula holder can be attached to the cannula to help securely hold the cannula to the cannula connector. The cannula holder can include a first clasp that receives and embraces the cannula while it is inserted onto the connector. The cannula holder can also include a second clasp for fastening the cannula holder to the connector.

Turning to FIGS. 1-6, a ventricular assist device 100 for assisting in pumping blood to and from a heart and that overcomes one or more of the problems described in this document is depicted. The ventricular assist device 100 may include a pump housing 110, a housing fastener 120, a one-way valve 130 (see, for example, FIG. 3), a cannula connector 140, a sac 150 (see, for example, FIG. 6), a pneumatic connector 160 (which may be part of a quick connect/disconnect fitting), an airflow channel 161 (see, for example, FIG. 3), a cannula holder 170, a torqueable wrench 180, and/or a purge device 190 (see, for example, FIG. 6). These components, individually or in combination, can play a role for a convenient and safe structure of a ventricular assist device 100. For example, the cannula holder 170 and the cannula connector 140 can help prevent axial movement, lateral (for example, crosswise) movement, or both types of movement of a cannula connected to the ventricular assist device 100. The cannula holder 170 can be easily installed, for example, by hand, before or after connecting the cannula to the cannula connector 140. The airflow channel 161 can help distribute air homogeneously inside the ventricular assist device 100 to consistently and homogeneously distribute positive or negative air pressure to a sac 150 in the ventricular assist device 100. The torqueable wrench 180 can be used to avoid damaging the pump housing 110 by notifying a user when the torque limit of a housing fastener 120 on the pump housing threads is reached. In addition, the purge device 190 may not only help purge trapped bubbles in the sac 150 before implanting the cannula, but it may also work as a guide to help keep the cannula straight in relation to the ventricular assist device 100. Therefore, the various features of the example ventricular device 100 can help overcome various problems associated with prior ventricular assist devices.

Figure 2:
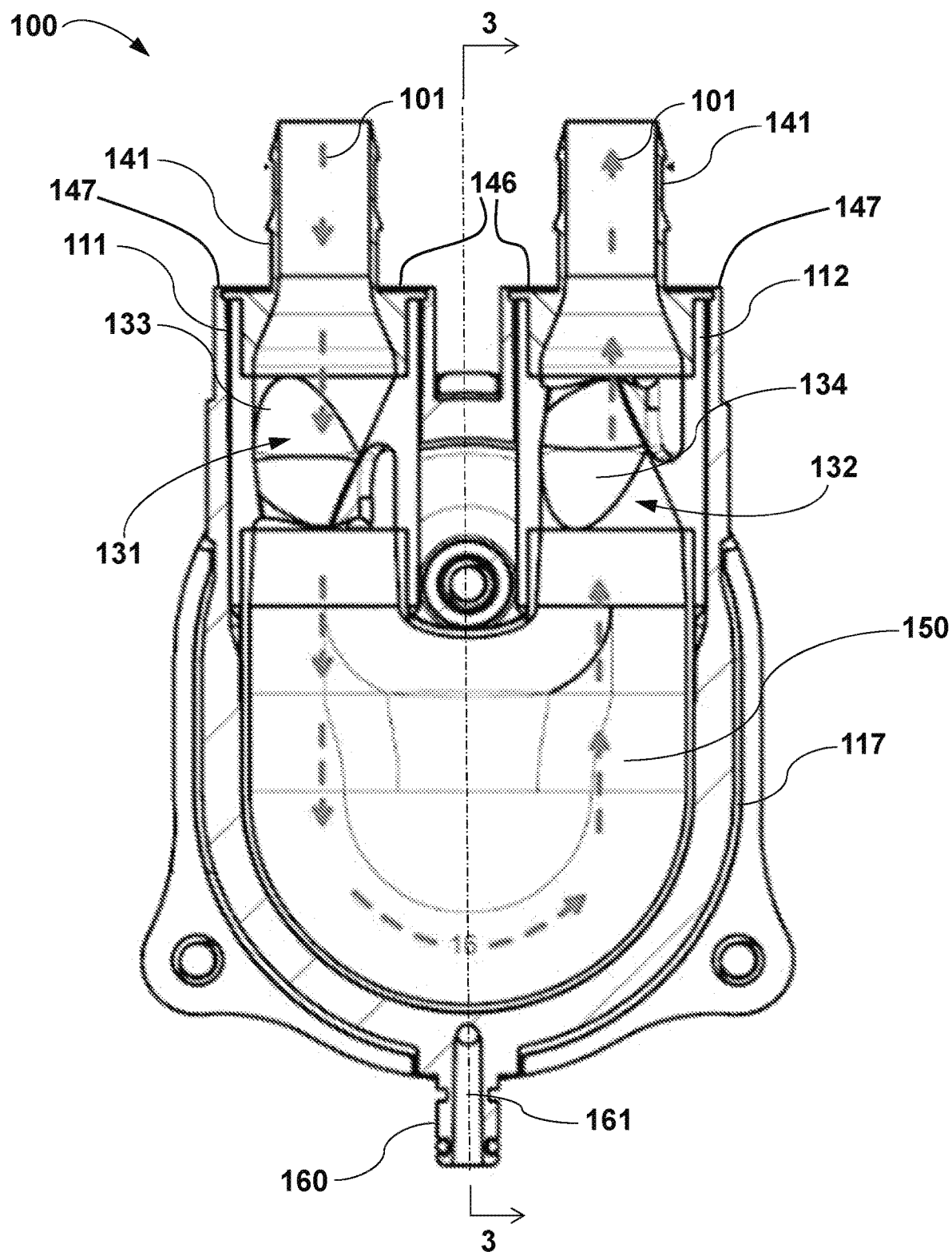
FIG. 2 is a top, cross-sectional view of the ventricular assist device shown in FIG. 1.
Figure 3:
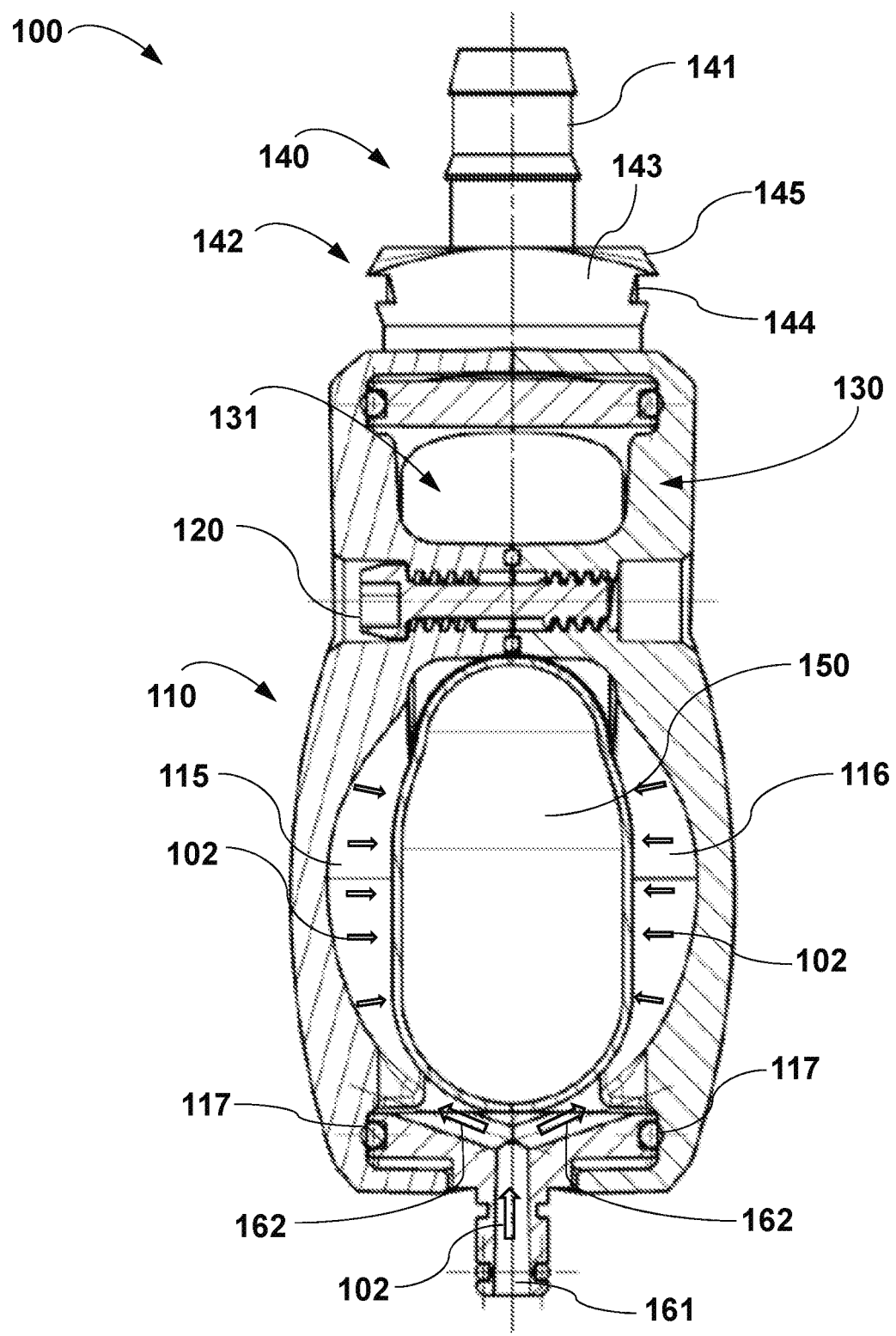
FIG. 3 is a cross-sectional view of the ventricular assist device shown in FIG. 2 taken along line 3-3.
Figure 6:
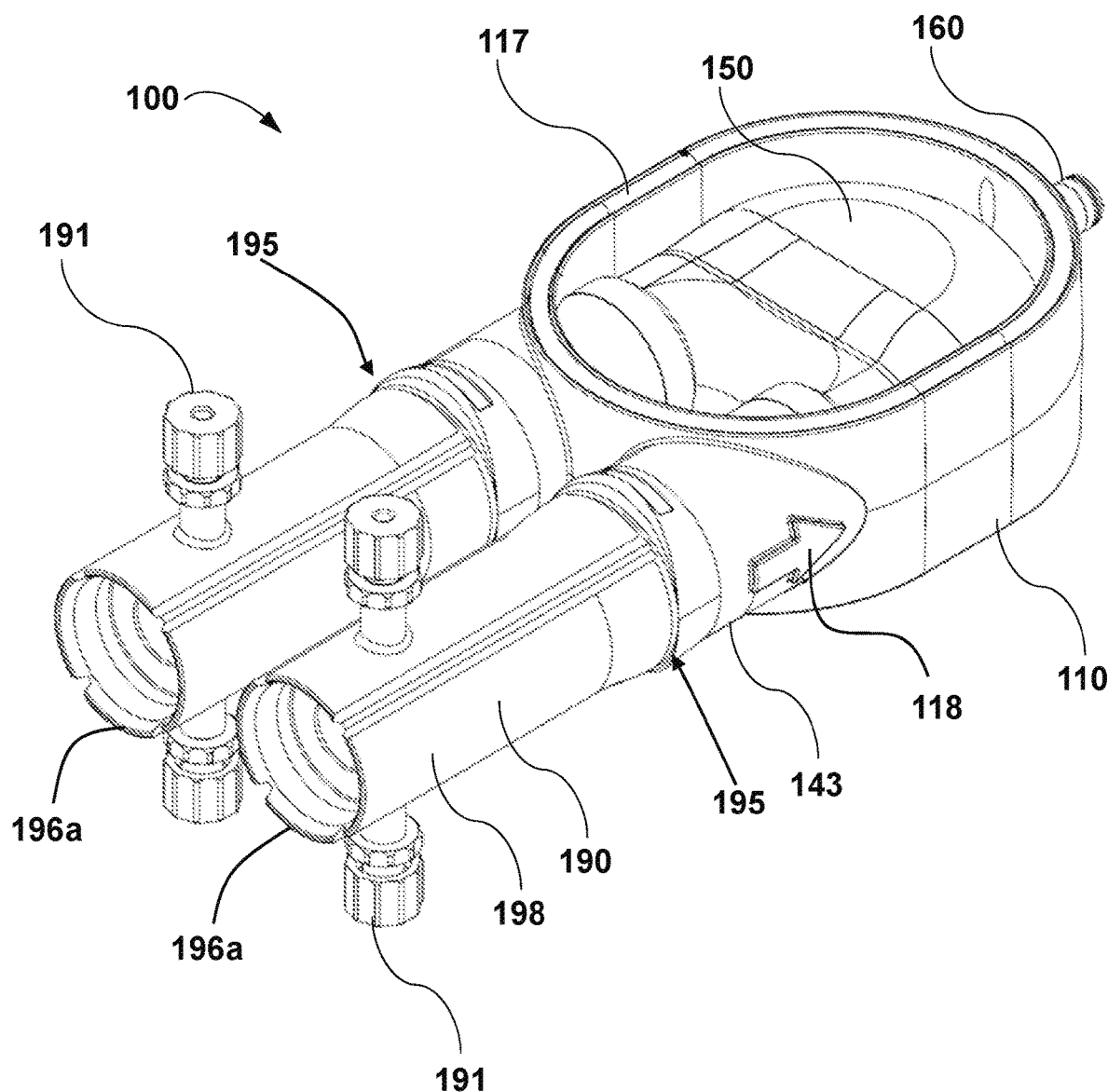
FIG. 6 is a perspective view of a ventricular assist device with two attached purge devices according to another embodiment of the present disclosure.
Figure 7:
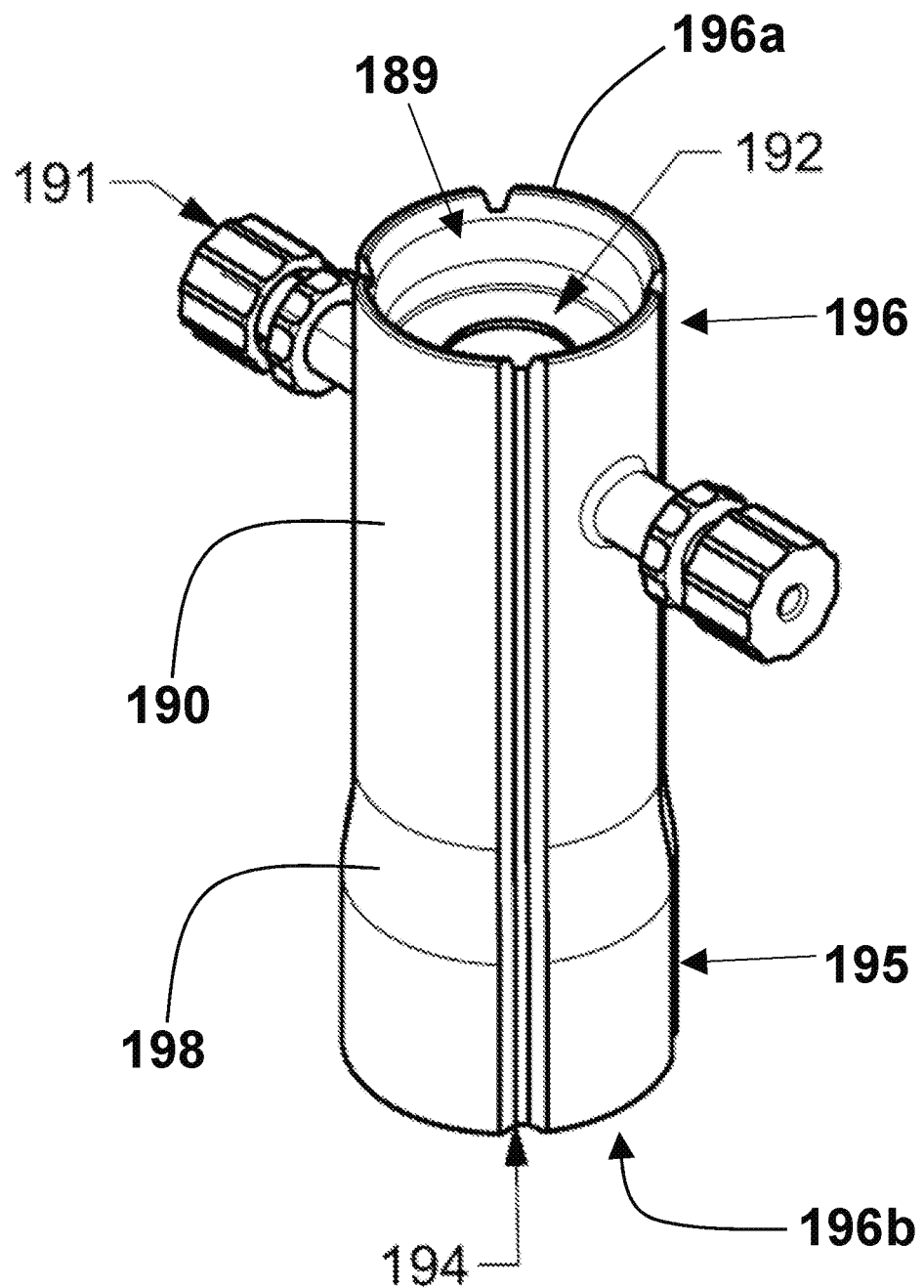
FIG. 7 is a perspective view of one of the purge devices shown in FIG. 6.
Figure 8:
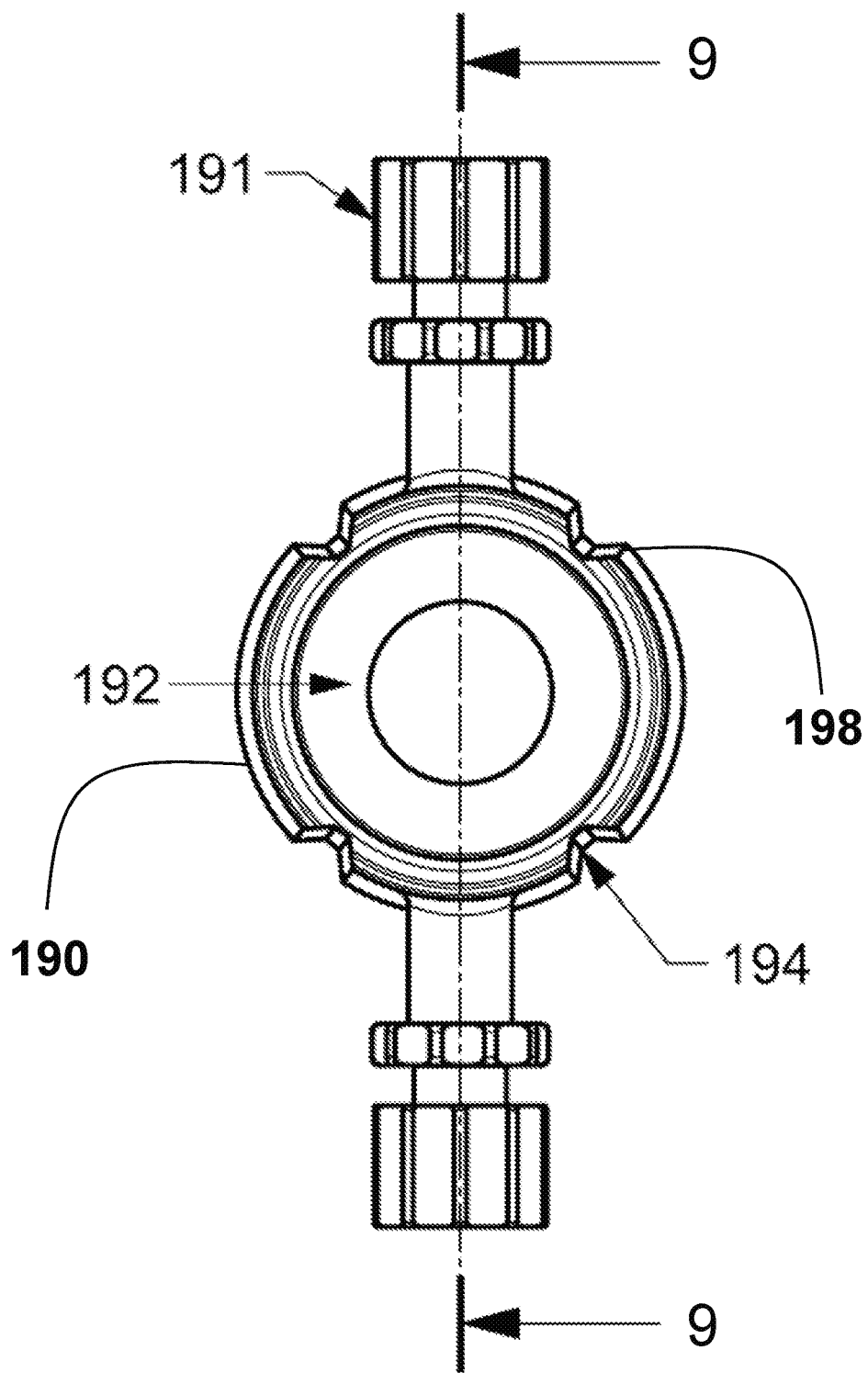
FIG. 8 is a top plan view of the purge device shown in FIG. 6.
Figure 9:
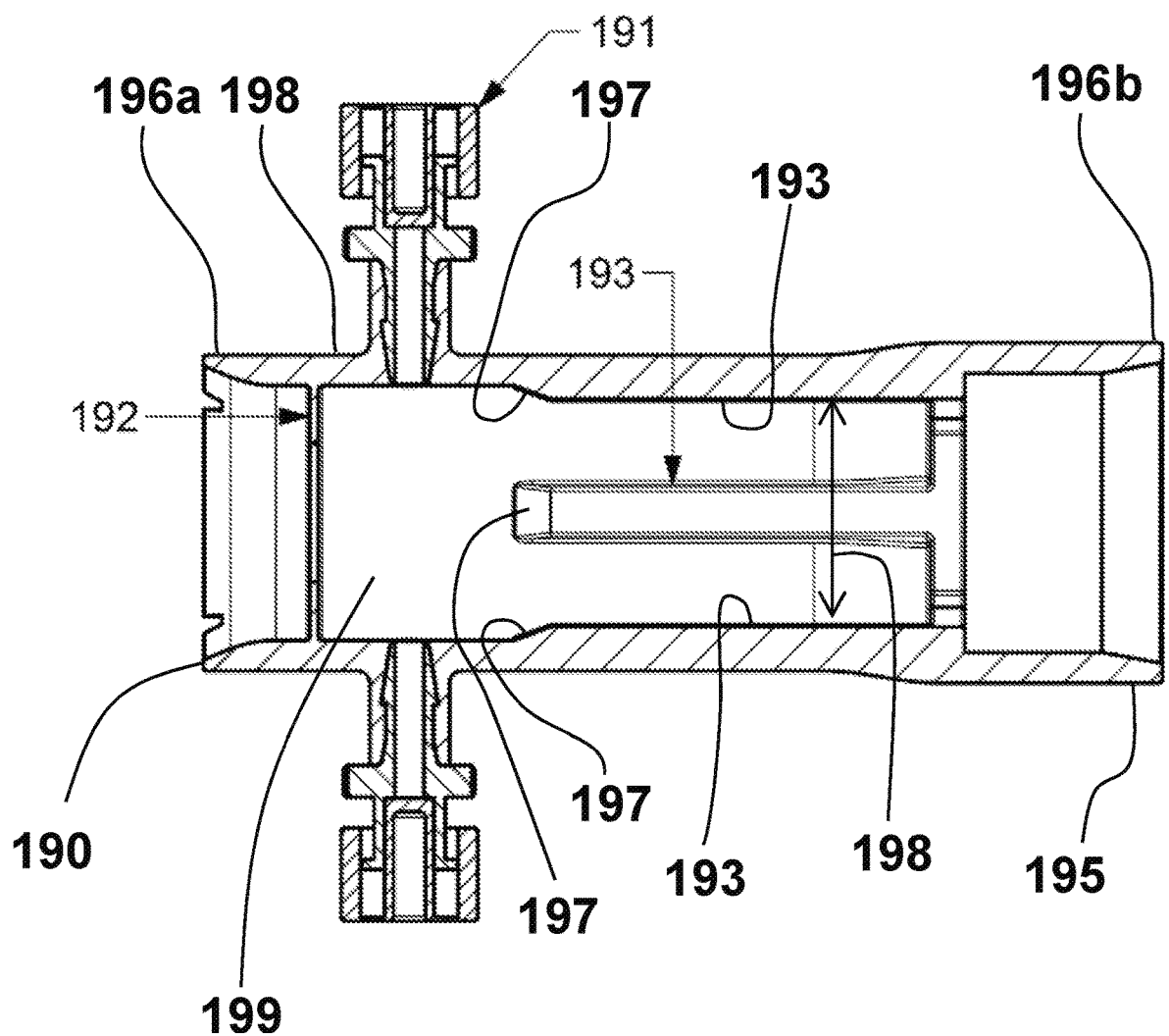
FIG. 9 is a cross-sectional view of the purge device shown in FIG. 8 taken along line 9-9.

As shown in FIGS. 1-3, the pump housing 110 defines an interior chamber with a pump inlet 111 and a pump outlet 112. The interior chamber may be divided into two chamber portions 115 and 116 by the sac 150. The pump housing 110 may include two housing halves 113 and 114 that fit together, which for convenience may be referred to as upper housing half 113 and lower housing half 114. The two housing halves 113 and 114 fit together and make the interior chamber (115/116) airtight, Air enters and exits the interior chamber 115 and 116 through an airflow channel 161 and the airflow channel 161 can be used control the level of pressure in the interior chamber 115 and 116. An optional sealing component, for example gasket 117, may be positioned between the two housing halves 113 and 114. In alternate embodiments, the two housing halves may resemble a large housing assembly with a smaller top cover, such as depicted in FIG. 6, instead of the two housing halves 113 and 114 that are approximately equal in size. It is noted that in FIG. 6 the top cover that forms a seal with gasket 117 and helps define the interior chamber 116 is not depicted, thereby providing a view of sac 150.

One or more housing fasteners 120 may be used for fastening the two housing halves 113 and 114 together to be mechanically sealed. The housing fastener 120 may include a screw thread at an end of the housing fastener 120. The screw thread in the housing fastener 120 provides rotational and linear force into the pump housing 110. The screw thread in the housing fastener 120 may fit into an internal thread in the pump housing 110. While the number of housing fasteners 120 is depicted as being three, alternate embodiments utilize a different number of housing fasteners 120. Alternate embodiments utilize housing fasteners 120 that are not of a screw thread type provided that the type and number of housing fasteners 120 provide enough force for two housing halves 113 and 114 to be sealed without allowing air to escape through any location on the pump housing 110 other than the airflow channel 161. However, when more than tolerable force is applied by the housing fastener 120 to the pump housing 110, the pump housing 110 can be broken or damaged such that air in the internal chamber can leak through the damaged place of the pump housing 110.

Embodiments of the present disclosure include a torqueable wrench, which can be used to help facilitate a proper hermetic seal and to assist the surgeon when connecting the two or more sections with screw-type fasteners. In some embodiments the torqueable wrench can help prevent over-torqueing of the one or more housing fasteners 120, which can help prevent damaging or misshaping the pump housing and/or the gasket when the two or more sections are connected together using screw-type fasteners. For example, to help prevent damaging due to excessive force of the housing fastener 120 on the pump housing 110 a torqueable wrench 180 may be used to fasten the housing fastener 120 to the pump housing 110 and limit the force on the pump housing 110. The torqueable wrench 180 facilitates a secure mechanical seal of the pump housing 110 by the one or more housing fasteners 120 and helps prevent a user from damaging the internal thread of the pump housing 110. The torqueable wrench 180 is configured to limit the torque that may be applied to a fastener 120. For example, when the torque limit is reached the torqueable wrench 180 can make a "click" sound. The torqueable wrench 180 can include a handle 181 to make maneuvering the torqueable wrench 180 easier during the pump housing closing process, in some embodiments the handle 181 is removable and can be reattached to the torqueable wrench 180 with only the force of the hands.

Referring to FIGS. 2 and 3, the one-way valve 130 disposed in the ventricular assist device 100 helps blood to move in only one direction through the ventricular assist device 100. The inlet side of the ventricular assist device 100 moves blood from the body of a user to the sac 150, and the outlet side of the ventricular assist device 100 moves blood from the sac 150 to the body of the user. The blood 101 comes into the ventricular assist device 100 from the body through the pump inlet 111 and goes into the body through the pump outlet 112. In the ventricular assist device 100, the blood 101 moves from the pump inlet 111 to the pump outlet 112 through the sac 150. The one-way valve 130 may include an inlet valve 131 (which in some embodiments may be referred to as a one-way inlet valve) and an outlet one-way valve 132 (which in some embodiments may be referred to as a one-way outlet valve). The inlet side of the ventricular assist device 100 may include an indicator, such as an inlet arrow 118, to help users easily identify the inlet side of the ventricular assist device 100. The outlet side of the ventricular assist device 100 may include an indicator, such as an outlet arrow 119, to help users easily identify the outlet side of the ventricular assist device 100.

The inlet valve 131 is positioned between the pump inlet 111 at one end of the inlet valve 131 and the sac 150 at the other end of the inlet valve 131. The inlet valve 131 may have three leaflets 133 for opening and closing the pump inlet 111. The three leaflets 133 are similar to and mimic the tricuspid valves of a human heart. When the three leaflets 133 are open, the blood 101 can move into the sac 150 through the pump inlet 111. When the three leaflets 133 are closed, the three leaflets 133 inhibit the blood 101 from flowing back to the body from the sac 150.

Similarly, the outlet valve 132 is positioned between the pump outlet 112 at one end of the outlet valve 132 and the sac 150 at the other end of the outlet valve 132. The outlet valve 132 may also include three leaflets 134 for opening and closing the pump outlet 112. When the three leaflets 134 are open, the blood 101 can move into the body from the sac 150 through the pump outlet 112. When the three leaflets 134 are closed, the three leaflets 134 inhibit the blood 101 from flowing back to the sac 150 from the body. In some embodiments the leaflets include memory material, and the opening and closing of the three leaflets 133 and 134 are possible due to memory of the material of the three leaflets 133 and 134.

Figure 4:
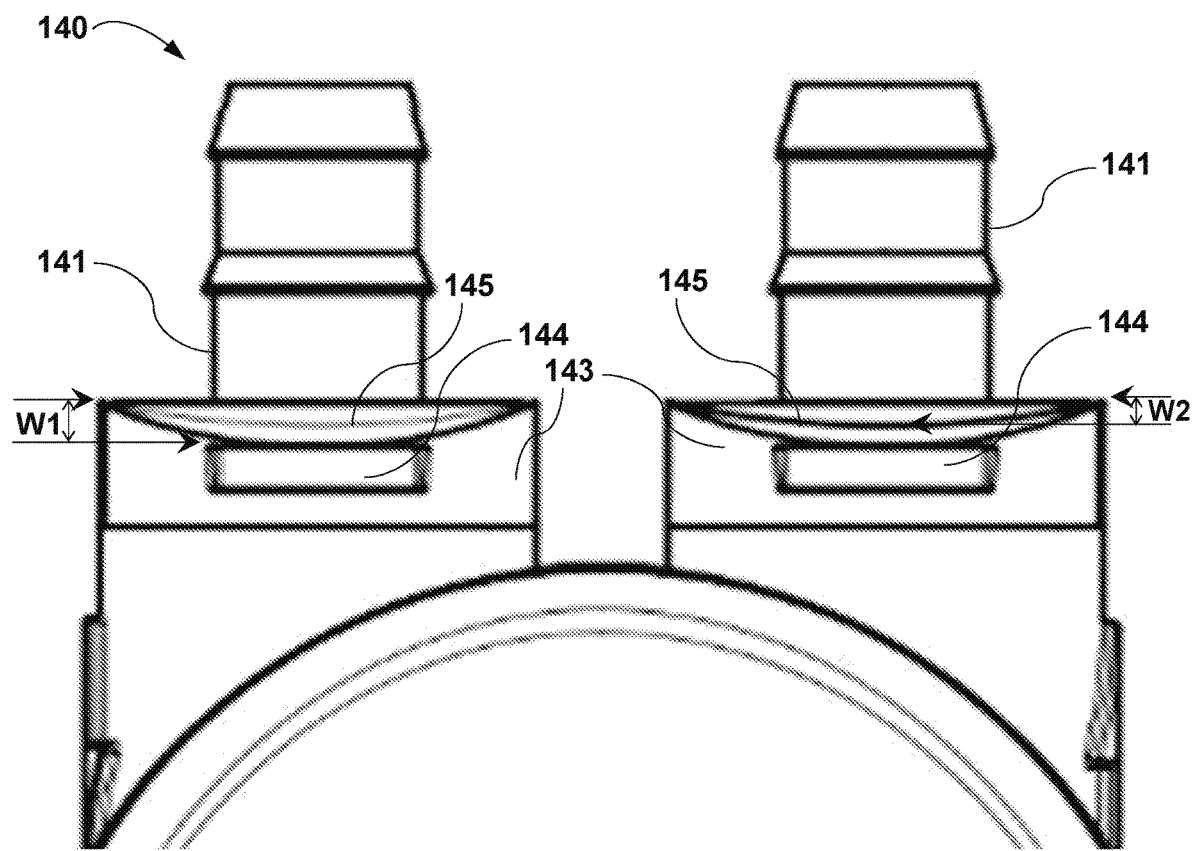
FIG. 4 is a fragmentary plan view of the ventricular assist device shown in FIG. 1.

In FIGS. 2 and 4, the cannula connector 140 may be connected to the pump housing 110, or may be integrally formed with the pump housing 110. In some embodiments the connector 140 may be a pair of connectors 140. One of the pair of connectors 140 may be connected to the pump inlet 111 and the other of the pair of connectors 140 may be connected to the pump outlet 112. Each connector 140 may be also be optionally connected to a cannula. The connector 140 may include a cannula connector 141, which is configured to be inserted into a cannula and which may protrude from the pump housing 110, and a pump housing connector 142, which is connected to the pump housing 110 for fastening the protruding cannula connector 141. The protruding cannula connector 141 may also be formed integrally as part of the pump housing 110 or may be a separate piece and not be a part of the pump housing 110.

The protruding cannula connector 141 may be substantially cylindrical in shape. However, in some embodiments the diameter of the end of the protruding cannula connector 141 that first meets the cannula when connecting the cannula connector 141 to a cannula may be smaller than the other part of the protruding cannula connector 141 to facilitate easy insertion of the protruding cannula connector 141 into the cannula. The protruding cannula connector 141 may have one or more flanges or protuberances, which may be in the middle portion of the protruding cannula connector 141, to inhibit the cannula from being easily removed, In embodiments where the protruding cannula connector 141 is a separate component from the pump housing 110, the end of the protruding cannula connector 141 that is connected to the pump housing 110 may be larger in diameter than other parts of the protruding cannula connector 141 to help fasten the protruding cannula connector 141 into an aperture in the pump housing 110. The protruding cannula connector 141 and other portions of the ventricular assist device 100, including the pump housing 110, may be made of stainless steel. However, the material to make the protruding cannula connector 141 and other portions of the ventricular assist device 100, including the pump housing 110, is not limited to stainless steel and may include one or more of polyvinyl chloride (PVC), polypropylene (PP), polyethylene (PE), polystyrene (PS) as well as nylon, polyethylene terephthalate (PET), polyimide (PA), polycarbonate (PC), acrylonitrile butadiene (ABS), polyetheretherketone (PEEK) and polyurethane (PU).

The pump housing connector 142 may be formed integrally as part of the pump housing 110 or may be a separate piece and not a part of the pump housing 110. The pump housing connector 142 may play a role in fastening the protruding cannula connector 141 to the pump housing 110 and preventing axial movement of the one-way valve 130. The pump housing connector 142 may include a connector body 143 connected to the protruding cannula connector 141, a cavity 144 on the connector body 143 and a strip 145 formed on the connector body 143 and disposed between the cavity 144 and the protruding cannula connector 141. The connector body 143 may be cylindrical in shape with one end of the connector body 143 (for example, one end circle of the connector body 143) connected to the protruding cannula connector 141. As shown in FIG. 1, the outer diameter of the connector body 143 may be larger than the outer diameter of the protruding cannula connector 141. The other end of the connector body 143 is connected to the pump housing 110. The cavity 144 is disposed on the outer surface of the connector body 143, which may be curved. In the embodiment illustrated in FIGS. 1 and 3 the cavity 144 is generally rectangular in shape with two generally parallel surfaces, for example, the top and bottom surfaces of cavity 144 as depicted in FIG. 3. However, the shape of cavity 144 is not limited to being generally rectangular provided the cavity 144 allows fastening of the cannula holder 170 to the pump housing 110.

The strip 145 that forms one side of the cavity 144 (the upper side of cavity 144 as depicted in FIG. 3) may be integrally formed with the connector body 143. In some embodiments the strip 145 is attached to the connector body 143 in a direction perpendicular to which the protruding cannula connector 141 extends from the pump housing 110. For example, the strip 145 may be attached on a curved surface of the connector body 143, The strip 145 may enclose the half of the curved surface of the connector body 143.

A width at a point of the strip 145 in a direction to which the protruding cannula connector 141 is extended may be different from a width at a different point of the strip 145. For example, as depicted in the example illustrated in FIG. 4 a width (W1) at one point of the strip 145 close to the cavity 144 in a direction to which the protruding cannula connector 141 extends from the pump housing 110 is wider than a width (W2) at another point of the strip 145 distant from the cavity 144. The width (W1) in the middle of the strip 145 is wide and tapers to thin points at each end. The cannula holder 170 is inserted at the thin points of the strip 145 and is fastened such that an end 176 of the cannula holder is inserted into the cavity 144 and an open area 177 of the cannula holder is holding tight as the open area 177 is being close to the middle of the strip 145 where the cavity 144 is disposed.

Figure 5:
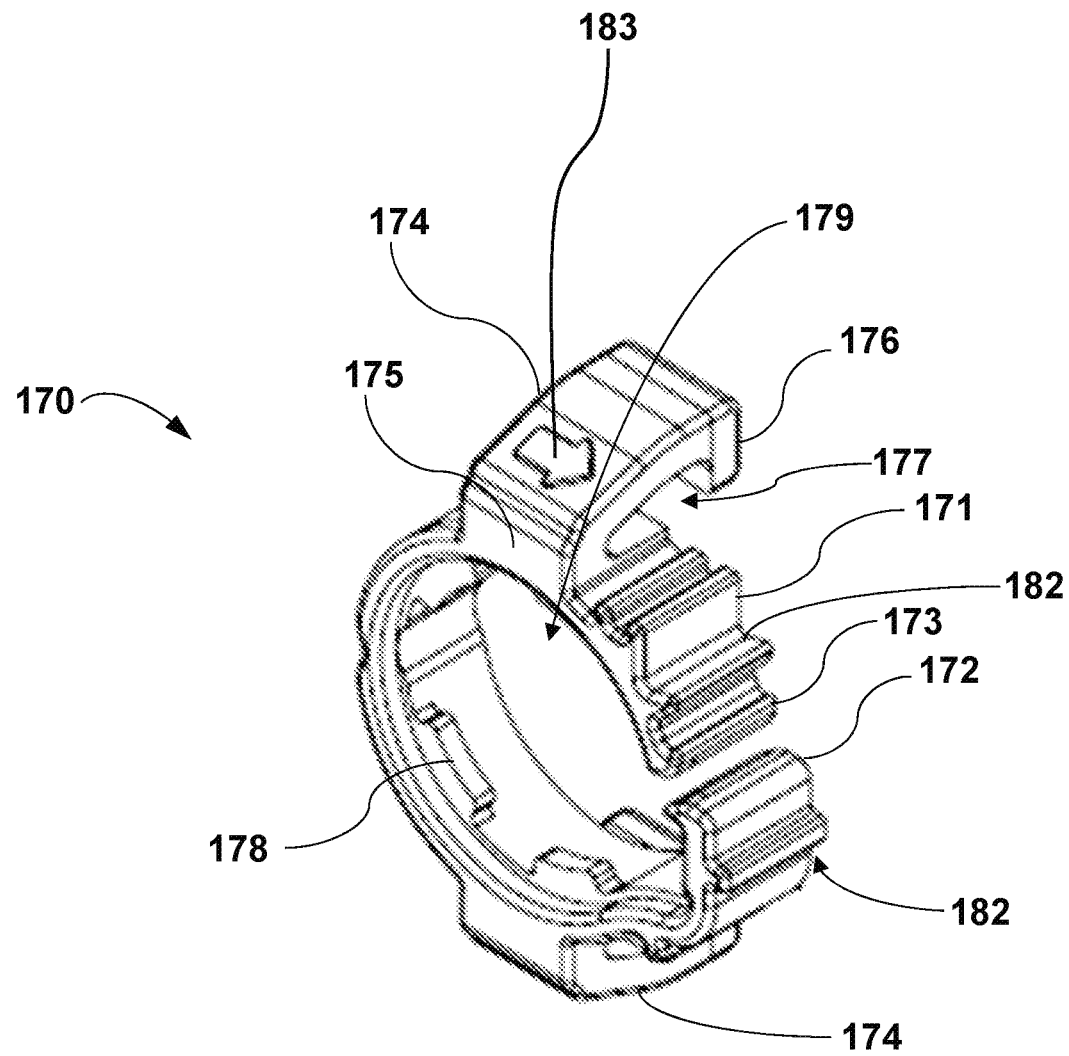
FIG. 5 is a perspective view of a cannula holder according to one embodiment of the present disclosure.

Depicted in FIGS. 1 and 5 is a cannula holder 170 (that can take the form of one or more clips or clasps) which is configured and adapted to fasten a cannula to a cannula connector 140, according to at least one embodiment of the present disclosure. The cannula holder 170 may include a first clasp 171 for fastening the cannula to the connector 140 and may also include one or more second clasps 174 for fastening the cannula holder 170 to the connector 140. Each of the one or more second clasps 174 can define a first end 175 and a second end 176, The first end 175 of the second clasp 174 can be connected to, and in the embodiment depicted in FIG. 5 is integrally formed with, the first clasp 171.

The first clasp 171 may be a non-closed (open) clip that substantially surrounds and encloses the protruding cannula connector 141. The first clasp 171 may be generally round in shape with two ends that can be separated to enclose the protruding cannula connector 141. The first clasp 171 may be configured to be opened and placed around the connector 141 either before or after the protruding cannula connector 141 has been inserted into the cannula. In some embodiments, the first clasp 171 may define a plane, such as a plane perpendicular to the blood flow direction 101 through the protruding cannula connector 141 when the first clasp 171 is connected to the protruding cannula connector 141 (which typically occurs when the first clasp 171 surrounds a cannula inserted onto the protruding cannula connector 141), and the one or more second clasps 174 can extend in a direction that is different than (for example, not parallel to, and in some embodiments substantially perpendicular to) the plane defined by the first clasp 171.

The cannula holder 170 may be configured to increase friction between the cannula and the connector 141, For example, the cannula holder 170 may be configured to embrace at least a portion of the cannula and increase the pressure between the cannula and the cannula connector 141, such as by exerting external pressure to the cannula. The shape of the first clasp 171 may be substantially circular, as depicted in FIG. 5, or it may be of other geometric shapes such as triangular, rectangular, square, pentagonal, hexagonal, octagonal, rhomboid, etc, The inside of the first clasp 171 may include at least one restraining member (for example, protuberance 178) which increases the pressure on the cannula for holding the cannula more tightly. Some embodiments include one or more protuberances 178 that are sized to fit within complimentary receptacles in the cannula, such as grooves in the cannula that may extend around the circumference of the cannula. The ability of the cannula holder 170 to hold a cannula to the cannula connector 140 can be enhanced when the one or more protuberances 178 are inserted into the one or more grooves in the cannula and the second clasps 174 are clipped to the cannula connector 140.

A first end 172 and second end 173 of the first clasp 171 can be configured to interlock with one another. For example, in at least one embodiment, such as the one depicted in FIG. 5, the first end 172 of the first clasp 171 is curved into a substantially inverted J-shaped (⌒) hook structure and the second end 173 of the first clasp is curved into a complimentary substantially upright J-shaped (J) hook structure when viewed in the orientation depicted in FIG. 5. The first end 172 of the first clasp 171 can be connected and fastened to the second end 173 of the first clasp 171 by engaging the complimentary hook structures with one another. When the first end 172 of the first clasp 171 is fastened to the second end 173 of the first clasp 171, the inner diameter of the round shape of the first clasp 171 is smaller than the outer diameter of the cannula, which holds the cannula tightly onto the protruding cannula connector 141.

One or both of the first end 172 and the second end 173 of cannula holder 170 can optionally include closure features that facilitate fastening the first end 172 and the second end 173 of the first clasp 171 together. For example, one or both of the first end 172 and the second end 173 of the first clasp 171 can include a closure surface 182, which may resemble a ledge, to enhance the ability of a user to close first clasp 171. As depicted in FIG. 5, the closure surfaces 182 are substantially flat, but in other embodiments the closure surfaces can be convex or have texture to enhance the user's ability to close the first clasp 171. In some embodiments the closure features are configured to be engaged by a tools, such as a pair of surgical tweezers, forceps, or pliers.

Some embodiments include more than one hook structures to allow adjustability. For example, the second end 173 of the first clasp 171 depicted in the embodiment shown in FIG. 5 defines a second substantially upright J-shaped (J) hook structure, which may also be described as a substantially upright U-shaped (U) hook structure) allowing for engagement of the substantially inverted J-shaped (⌒) hook structure to adjust the inner diameter of the first clasp 171 for differently (for example, smaller) sized connectors 141 and/or differently (for example, smaller) sized cannulas.

When a second clasp 174 is connected to a cannula connector 140, the second clasp 174 forms a mechanical connection with the pump housing 110 axially latching the cannula holder 170 to the pump housing 110. In embodiments were the connector 140, the pump housing connector 142, and/or the protruding cannula connector 141 are not integrally formed with but are connected to the pump housing 110, the axial latching of the second clasp 174 to the pump housing 110 may be via direct mechanical connection to the connector 140, the pump housing connector 142, and/or the protruding cannula connector 141. The second clasp can help prevent the first clasp 171 from slipping and the second clasp 174 can extend in a direction substantially parallel to the direction in which the protruding cannula connector 141 extends from the pump housing 110, which may be described as being in an axial direction.

The second clasp 174 may be fastened to the connector 140 by inserting the second end 176 of the second clasp 174 into the cavity 144. The second end 176 of the second clasp 174 is shaped to fit into the cavity 144 and, as depicted in FIG. 5, the second clasp 174 is a substantially C-shaped structure that is rotated by 90-degree (⋂), which roughly resembles a lower case Greek letter eta. An open area 177 defined by the second clasp 174 can accommodate the strip 145 when the second end 176 of the second clasp 174 is inserted into the cavity 144.

The strip 145 can facilitate easier connection of the cannula holder 170 to the connector body 143 by, for example, providing a ramp on which the second clasp 174 can slide before engaging cavity 144 as depicted in FIG. 4. In the depicted embodiment the strip 145 is blended into connector body 143 with the width (W1) at one point of the strip 145 close to the cavity 144 being wider than a width (W2) at another point of the strip 145 distant from the cavity 144. In other embodiments the strip 145 extends farther around, and in some embodiments completely around, the circumference of connector body 143 creating a chamfered appearance.

In alternate embodiments the first clasp 171 and the second clasp 174 are not integrally formed with one another. In these embodiments the first clasp 171 and the second clasp 174 may securely fasten to one another when installed. For example, when installed the second clasp 174 may be clipped or otherwise fastened to the first clasp 171 before, during or after the first clasp is connected to the cannula.

The cannula holder 170 can optionally include an indicator arrow 183 to assist the user with attaching the cannula holder 170 to a cannula and the pump housing 110. For example, as depicted in FIG. 1 the indicator arrow 183 can indicate the direction of the first clasp 171, which can help a user install the cannula holder 170 so that the first clasp 171 is positioned on the outside of the pump housing connector 142, in other words, on the side of the pump housing connector 142 that is away from the other pump housing connector 142 that the cannula holder 170 is not attached. By having both first clasps 171 located on the outside of their respective pump housing connectors, the first clasps 171 of the cannula holders 170 will not be located in the small space between the pump housing connectors where they can interfere with one another and be located in a position that is difficult for a user to manipulate.

In use, a cannula may be fastened to the cannula connector 140, and fastened to the pump housing 110, by (in no specific order unless so stated):

- inserting a cannula through an open area 179 of the cannula holder 170, and optionally positioning the indicator arrow 183 so that the indicator arrow 183 will be pointed to the outside of the connector body to which the cannula holder 170 will be connected and away from the connector body 143 to which the cannula holder will not be connected;
- inserting the protruding cannula connector 141 into the cannula until the end tip of the cannula is proximal to the strip 145;
- if the cannula has not already been inserted through the open area 179 of the first clasp 171, separating the first end 172 and the second end 173 of the first clasp 171 and placing the first clasp 171 around the cannula;
- moving the first clasp 171 toward the connector body 143 with first clasp 171 surrounding protruding cannula connector;
- in embodiments where the cannula holder 170 includes one or more restraining members (for example, one or more protuberances 178) engaging the one or more protuberances 178 with complimentary receptacles (for example, grooves) on the cannula;
- in embodiments where the connector body 143 includes a groove 144, inserting the one or more second ends 176 of the one or more second clasps 174 into the one or more cavities 144, which may be facilitated by optionally sliding the one or more second ends 176 of the one or more second clasps 174 on the one or more strips (ramps) 145 making it easier to insert the one or more second ends 176 into the one or more cavities 144 to help hold the cannula holder 170 securely to the cannula connector 140;
- closing the cannula holder 170 by moving the first end 172 and the second end 173 toward one another, which may be accomplished using a user's fingers or by using a hand tool, such as forceps, tweezers, pliers, or the like; and
- engaging the substantially inverted J-shaped (⌐) hook structure on the first end 172 and the complimentary substantially upright J-shaped (J) hook structure on the second end 173, which may be accomplished using a user's fingers or by using a hand tool, such as forceps, tweezers, pliers, or the like.

It should be noted that the first clasp may also be used as a clamp for a section of cannula that is distal to the protruding cannula connector 141, such as an exposed cannula section that is outside of the abdominal or thoracic cavity.

As shown in FIGS. 2, 3, and 6, the sac 150 is disposed in an interior cavity of pump housing 110 and adjacent chambers 115 and 116. The sac 150 may be a flexible membrane and may have mechanical memory. The sac 150 is connected to the pump inlet 111 and the pump outlet 112. In use, the blood 101 comes into the sac 150 through the pump inlet 111, typically during systole, and is ejected from the sac 150 to the pump outlet 112, typically during diastole.

In FIGS. 2 and 3, the airflow channel 161 is disposed at an end of the pump housing 110 for moving air into or out from the interior chambers 115 and 116 to pressurize and depressurize the sac 150, respectively. A connector 163 can be included to connect the airflow channel 161 to the environment external to the ventricular assist device 100. For example, the connector can connect the airflow channel 161 to an external pressure source, which can generate pneumatic pulses to increase and decrease pressure within the first space 115 and/or the second space 116, which in turn increases and decreases the pressure on the sac 150.

The airflow channel 161 may be positioned at an end of the pump housing 110 which is opposite to the end at which the pump inlet 111 and the pump outlet 112 are disposed. However, the position of the airflow channel 161 is not limited to the end of the pump housing 110 if the airflow channel 161 can move air into and out from the interior chambers 115 and 116, and in particular if the airflow channel 161 can homogeneously move the air into and out from the interior chambers 115 and 116. The airflow channel 161 may optionally be bifurcated into two conduits 162, which may be symmetrical, to aid in distributing the pneumatic pressure in a homogeneous manner between the first space 115 (located between a side 113 of the pump housing 110 and the sac 150) and a second space 116 (located between an opposite side 114 of the pump housing 110 and the sac 150). Having an equal pressure exerted on the sac 150 from the two chambers 115 and 116 assists in efficiently pumping the body fluid and helps decrease wear and tear on the sac 150 and the components of the ventricular assist device 100. One of the two conduits 162 may be connected to the first space 115 and the other of the two conduits 162 may be connected to the second space 116. The airflow channel 161 may be formed between the two housing halves 113 and 114.

Depicted in FIGS. 6-9 is a purge device 190, which can be used to assist in connecting a cannula to the ventricular assist device 100 and removing trapped bubbles from inside the sac 150. The purge device 190 includes a purge device body 198 defining an inner cavity 189 and two open ends 196a and 196b. The purge device 190 may be connected to the connector body 143 and optionally includes one or more Luer ports 191, one or more membranes 192, one or more guide channels 193 and one or more grooves 194. The Luer ports 191 may be used to assist in removing trapped bubbles from the device.

The optional membrane 192 is flexible and snugly fits around a cannula connected to the cannula connector 140 forming a seal around the cannula. The membrane 192 inhibits environmental air from getting inside the purge device 190 and inhibits fluid inside the purge device 190 (for example, a saline solution) from leaking to the outside of the purge device 190. The sealing function of membrane 192 can be particularly useful during assembly of the ventricular assist device 100.

The guide channels 193 are located in the interior of the purge device 190 and protrude from the inner wall of the purge device 190. One or more of the guide channels 193 can include a ramp portion 197 to assist the cannula with engaging the guide channels 193. The guide channels center the cannula and hold the cannula away from the inner surface 199 of the purge device 190 while presenting a contact surface for the cannula that is substantially less than embodiments in which the entire circumference of the inner surface 199 of purge device 190 is decreased to be being approximately equal to the outer circumference of the cannula. The distance 198 between the guide channels 193 is approximately equal to the outer diameter of the cannula. The guide channels 193 assist with straightening, guiding and supporting (for example, adding to the rigidity of) a cannula as the cannula is inserted into the purge device 190 and connected to the ventricular assist device 100.

In some embodiments the end 195 of the purge device 190 that connects to the ventricular assist device 100 is expandable and can expand to embrace connector body 143 within end 195 and form a fluid tight seal with connector body 143.

The one or more grooves 194, which are typically thin, assists with easy removal of the purge device 190 after the purging process. The groove 194 provides a thin location where cutters may be used to easily cut the purge device 190. Some embodiments include two or more grooves 194 to give the user options in where to cut the purge device 190 and/or to help separate each purge device 190 into two or more sections making it easier to remove the purge device 190. The purge device 190 is optionally made in a translucent material to assist a user in finding and purging bubbles.

Figure 10:
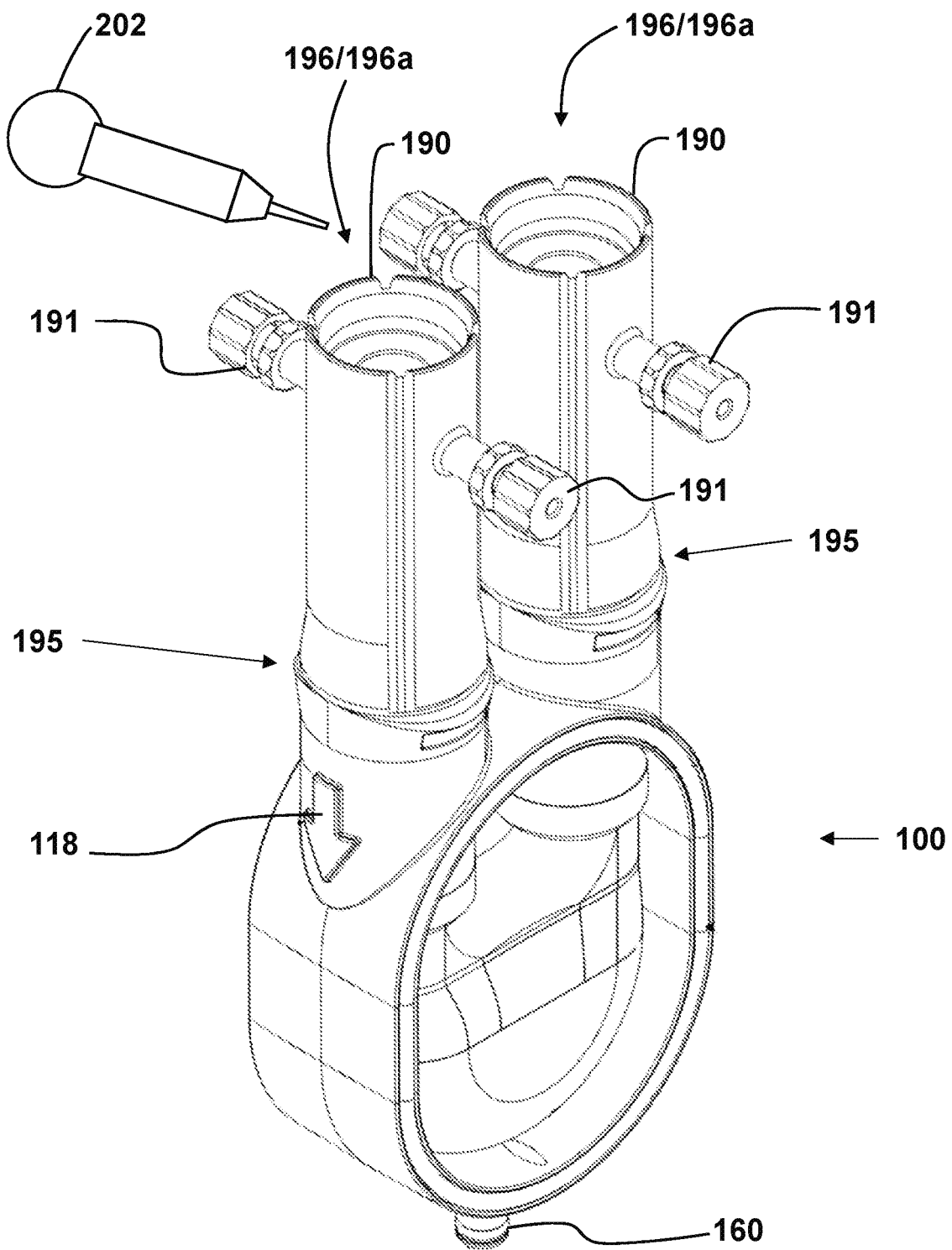
FIG. 10 is a perspective view of a ventricular assist device with two attached purge devices and a syringe for adding fluid according to embodiments of the present disclosure.

In use, a user attaches one or more purge devices 190 to the assembled ventricular assist device 100 as shown in FIG. 10. While the ends 195 of the purge devices 190 that engage with the ventricular assist device 100 are shown in FIGS. 6 and 10 as abutting edges 147 of connector body 142 (edges 147 are depicted in FIGS. 1 and 2), in other embodiments the VAD engagement ends 195 of the purge devices 190 extend past edges 147 and surround connector body 142, for example surrounding strips 145 and cavities 144 of connector body 142. The purge devices 190 may be made of flexible material so that each purge device 190 expands to fit over the pump housing connector body 142 and forms a liquid tight seal with the pump housing connector body 142.

Once the one or more purge devices 190 are connected to the ventricular assist device 100, a user can attach one or more cannulas 206 connected to a patient to the ventricular assist device 100. However, before attaching the ventricular assist device 100 to a patient, it can be advantageous to add fluid to the ventricular assist device 100 prior to connecting the ventricular assist device 100 to a patient. As shown in FIG. 10, a user may add fluid to the ventricular assist device 100 using a fluid administering device such as syringe 202. One manner of adding fluid includes positioning the ventricular assist device 100 with the openings of the purge devices 190 above the ventricular assist device 100, such as depicted in FIG. 10. A user may then use a liquid administering device liquid administering device (for example, syringe 202, which in one embodiment is an Aseptic syringe) to fill the ventricular assist device 100 with liquid, such as a medical saline solution. In one example embodiment the user fills the ventricular assist device 100 with saline solution until the level of the saline solution is above the Luer ports 191, and in some embodiments above the membrane 192, on both sides of the ventricular assist device 100.

It is common for gas bubbles (for example, air bubbles) to form and adhere to the inner walls of the ventricular assist device 100 and the purge devices 190 while adding liquid to the ventricular assist device 100. Because these gas bubbles can pose a danger to a patient if they are present when the ventricular assist device 100 is connected to the patient (such as being connected to a cannula that is connected to a patient's heart), advantages are realized by removing the gas bubbles from the ventricular assist device 100.

Figure 11:
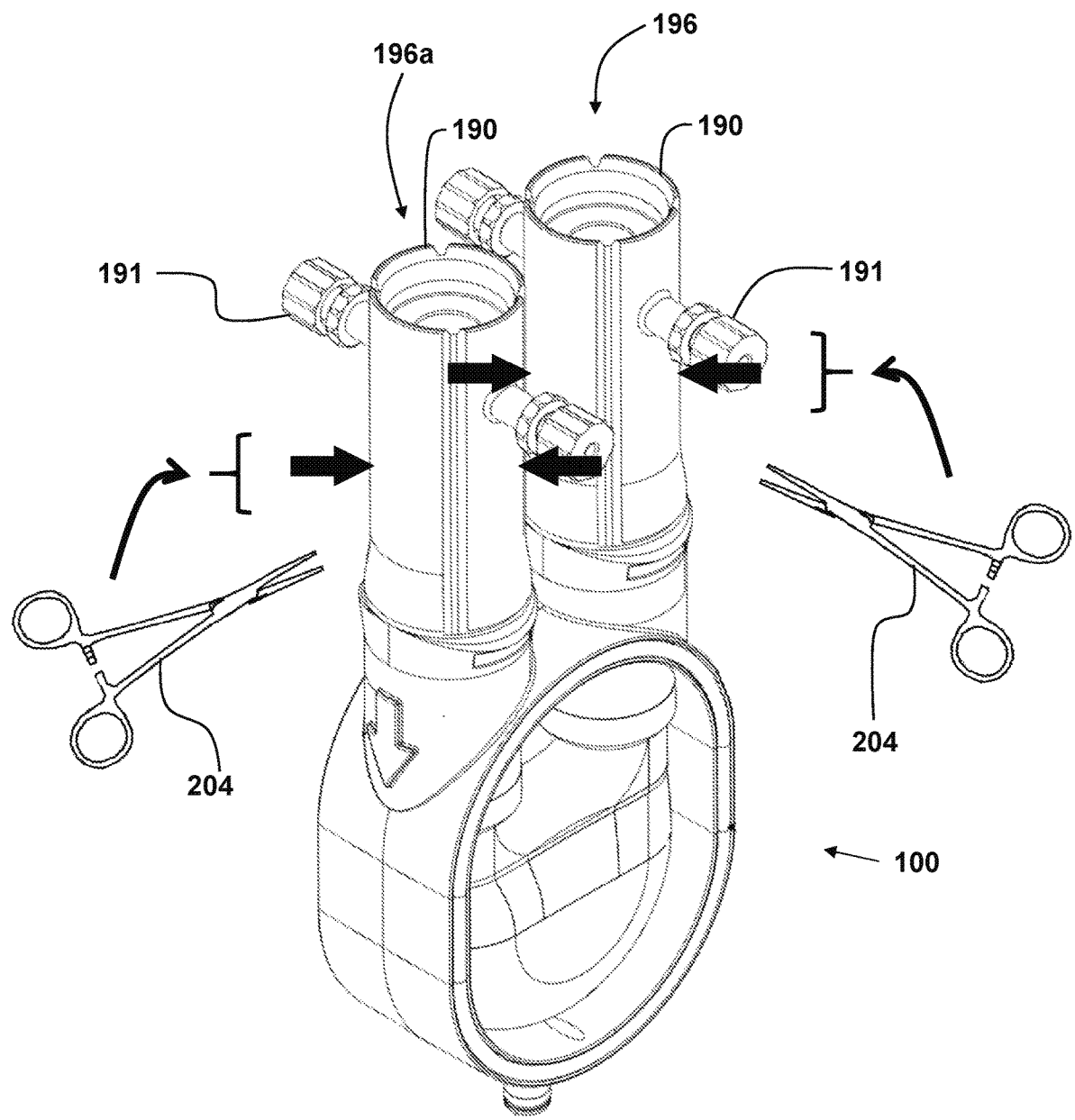
FIG. 11 is a depiction of locations where clamping devices can be attached the ventricular assist device and two attached purge devices of FIG. 10 to facilitate the purging of gas bubbles from the ventricular assist device according to embodiments of the present disclosure.
Figure 12:
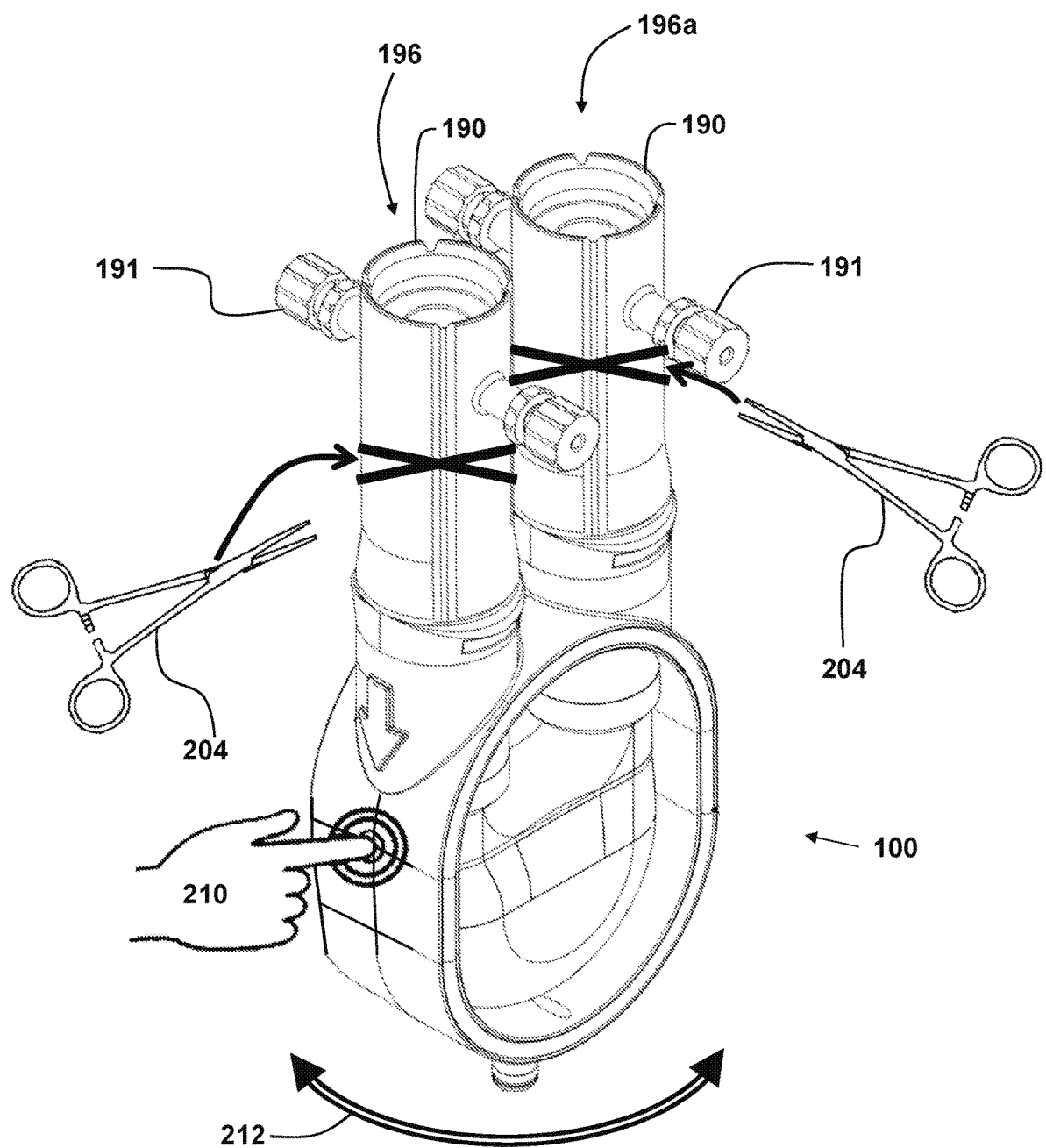
FIG. 12 depicts the removal of gas bubbles from the ventricular assist device and two attached purge devices of FIG. 10 according to embodiments of the present disclosure.

One example embodiment that may be used for removing gas bubbles from inside ventricular assist device 100 is depicted in FIGS. 11 and 12. To remove the gas bubbles a user may close the open ends (for example, open ends 196a) of the one or more purge devices 190 to hold the liquid in the ventricular assist device 100 with attached purge devices 190 while being tilted, rotated and/or tapped as depicted in FIG. 12. A clamp (for example, forceps 204, which in one embodiment are Rochester Pean curved clamps or similar) or another type of pinching device may be used to pinch the two purge devices 190 below the Luer ports 191 to close the exits of the purge devices 190 after the ventricular assist device 100 with the purge devices 190 attached is filled with fluid.

Once the exits of the purge devices 190 are closed as depicted in FIG. 12, gas bubbles adhering to the inner surfaces of ventricular assist device 100 may be loosened from the inner surfaces of ventricular assist device 100 by, for example, taping 210 (which may be done by hand or by using a tapping instrument such as a surgical device), rotating and/or tilting (represented by direction arrow 212) the ventricular assist device 100. By appropriately rotating and/or tilting the ventricular assist device 100 the user can guide the bubbles into one of the purge devices 190, such as into the purge device 190 attached to the outlet side of the ventricular assist device 100. In some embodiments it is advantageous to guide the bubbles into the purge device 190 attached to the outlet side of the ventricular assist device 100, For example, since the outlet valve 132 is oriented to permit flow from the ventricular assist device 100 to the purge device 190 (and inhibit flow from the purge device 190 to the ventricular assist device 100), the bubbles can flow relatively easily from the ventricular assist device 100 to the purge device 190 through the outlet valve 132. However, since the inlet valve 131 is oriented to permit flow from the purge device 190 to the ventricular assist device 100 and inhibit flow from the ventricular assist device 100 to the purge device 190, it is difficult for the bubbles to flow from the ventricular assist device 100 to the purge device through the inlet valve 131.

After moving the gas bubbles into one or more of the purge devices 190, a user may then open the ends of one or both of the purge devices 190 (such as by unclamping one or both of the purge devices 190) to allow the gas in the gas bubbles to escape and, if desired, add more liquid and repeat the process of adding fluid, closing the open ends (for example, open ends 196a) of the one or more purge devices 190, dislodging and moving the gas bubbles to one or both purge devices 190, and releasing the bubbles from the one or more purge devices 190 until there are no bubbles left in the ventricular assist device 100 or the one or more purge devices 190. Once the liquid in the ventricular assist device 100 and the one or more purge devices 190 is purged of gas bubbles, the user may attach a cannula 206 to each of the one or more ventricular assist devices 100.

To connect the ventricular assist device 100 to a patient, such as to one or more cannulas 206 connected to a patient, a user may fill a cannula 206 with liquid and close the end of the cannula 206, such as with a clamp (for example, forceps 204), with a sufficient length of cannula 206 extending beyond the forceps 204 to enable the end 207 of the cannula 206 to be inserted a sufficient distance to engage the cannula connector 141 without the forceps 204 interfering with the insertion. In at least one example embodiment, a cannula 206 is first attached to the inlet side of the ventricular assist device 100, which may be indicated by inlet arrow 118.

Figure 13:
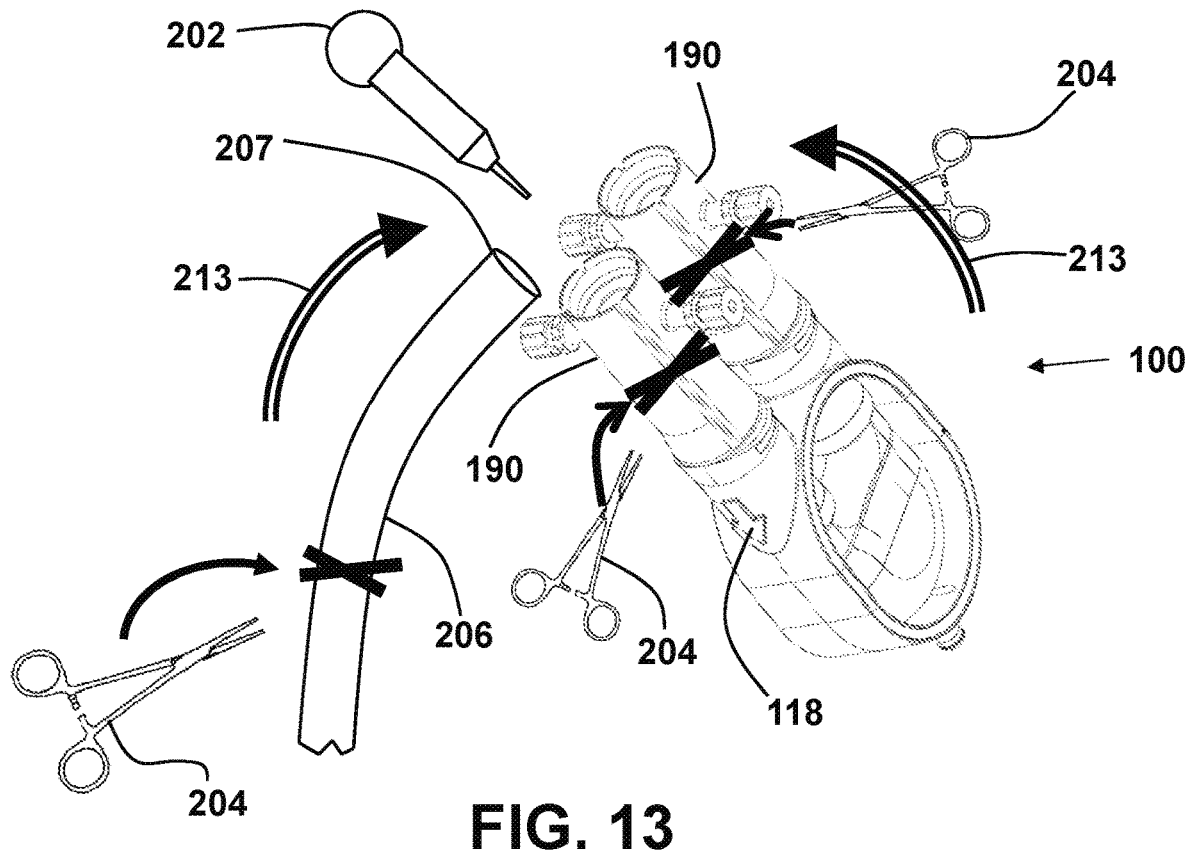
FIGS. 13 and 14 depict the connection of a cannula to the ventricular assist device and the two attached purge devices of FIG. 10 according to embodiments of the present disclosure.
Figure 14:
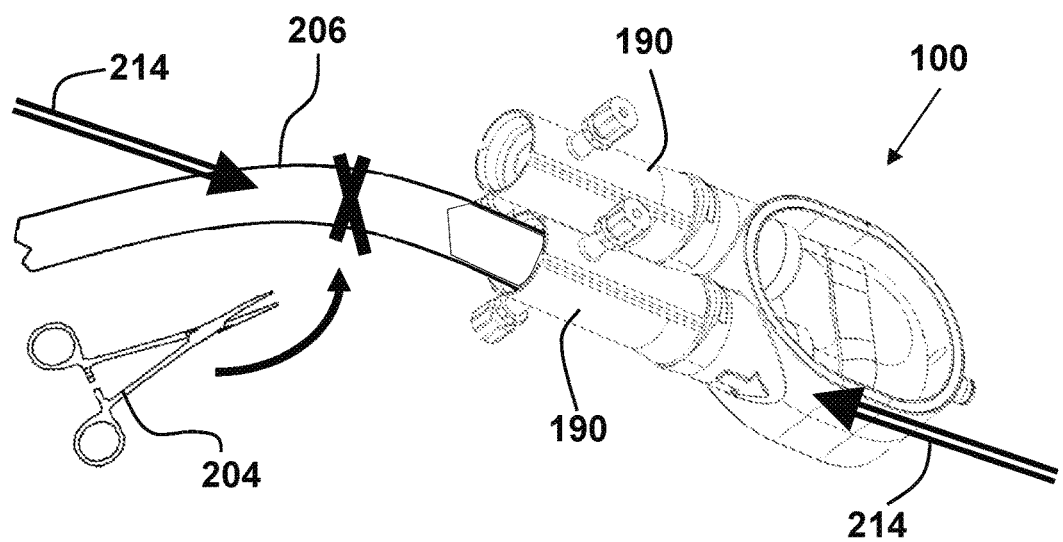

Since the end of the cannula 206 can be flexible, it can be bent to meet the opening of the purge device 190 as shown in FIGS. 13 and 14. The user may then insert the cannula 206 into the purge device 190 and move the end 207 of the cannula 206 down the purge device 190 until the cannula 206 engages with the abutment surface 146 of the cannula connector 140. See, FIG. 1 for a depiction of abutment surfaces 146. The cannula 206 is considered to be fully engaged with the ventricular assist device 100 when the end 207 of the cannula 206 contacts abutment surface 146.

One manner of inserting the cannula 206 into the purge device 190 is to tilt the purge device 190 (and optionally the ventricular assist device 100), for example, approximately 20 to 40 degrees from vertical, position the end of the cannula 206 adjacent the opening to the purge device 190, optionally bend the cannula 206 to insert it into the end of the purge device 190, continue rotating both the purge device 190 (with the ventricular assist device 100 connected) and the cannula 206 toward one another until the cannula 206 is inserted into the end of the purge device 190. Syringe 202 may be used to add liquid to the gap between the cannula 206 and the purge device 190 as the cannula 206 and the purge device 190 are connected. The ventricular assist device 100 and the cannula 206 can be tilted toward one another as depicted by direction arrows 213 in FIG. 13 and the end of the cannula 206 can be inserted into purge device 190 while optionally continuing to add fluid with syringe 202. Once the end of the cannula 206 is inserted into the end of the purge device 190, force may be applied to the cannula 206 and the ventricular assist device 100 in directions 214 as depicted by direction arrows 214 in FIG. 14 and the cannula 206 may be moved down the inside of purge device 190 until the cannula 206 engages with the cannula connector 141 and, optionally, end 207 of cannula 206 contacts abutment surface 146 of pump housing connector 142.

Each of the clamps (for example, forceps 204) may be removed during the process of inserting the cannula 206 into the purge device 190. In one example, the clamp attached to the purge device 190 is removed once the end of the cannula 206 in inserted into the open end 196a of purge device 190 and before the cannula 206 is moved to engage the cannula connector 141. In another example, the clamp attached to the purge device 190 is removed before the end 207 of the cannula 206 is inserted into the open end 196a of the purge device 190. In still another example, the clamp attached to the cannula 206 is removed before the end 207 of the cannula 206 is inserted into the purge device 190, while in still another example the clamp attached to the cannula 206 is removed after the end 207 of the cannula 206 is inserted into the purge device 190.

Since the purge device 190 forms a fluid tight seal with the ventricular assist device 100, the purge device 190 can serve as an extension of the fluid reservoir inside the ventricular assist device and can facilitate connection of a cannula to the ventricular assist device 100 without introducing gas bubbles into the ventricular assist device 100. One advantage of connecting the one or more cannulas 206 to the ventricular assist device utilizing the one or more purge devices 190 is that likelihood of having gas bubbles introduced into the one or more cannulas 206 is minimized, if not eliminated.

Figure 15:
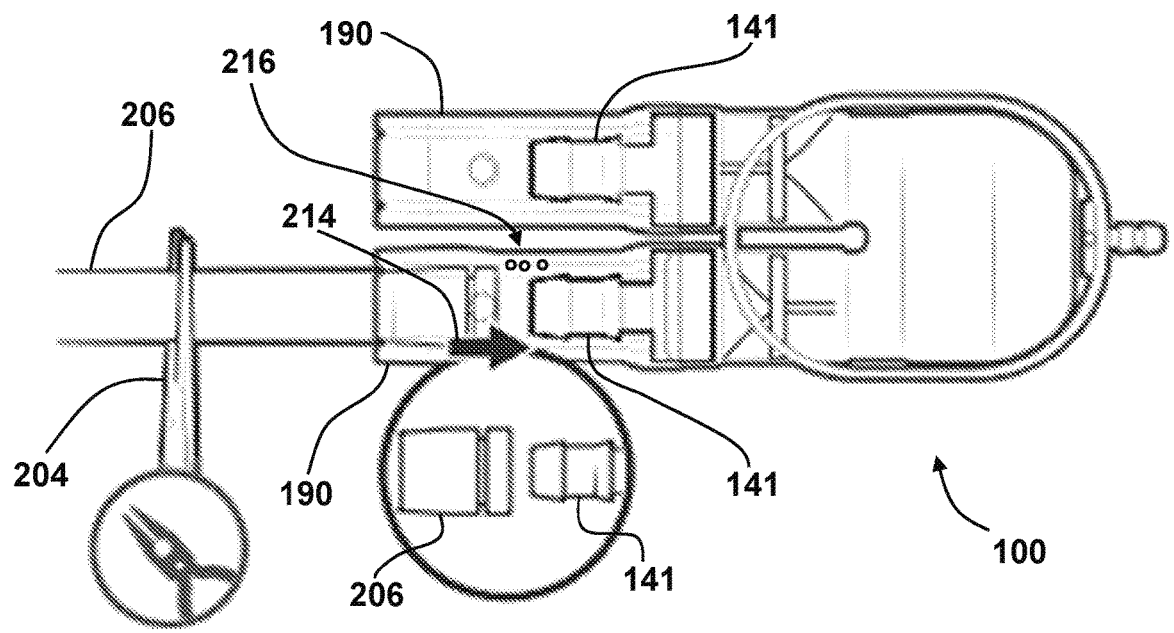
FIGS. 15 and 16 depict the removal of air bubbles from the ventricular assist device and the two attached purge devices of FIG. 10 according to embodiments of the present disclosure.
Figure 16:
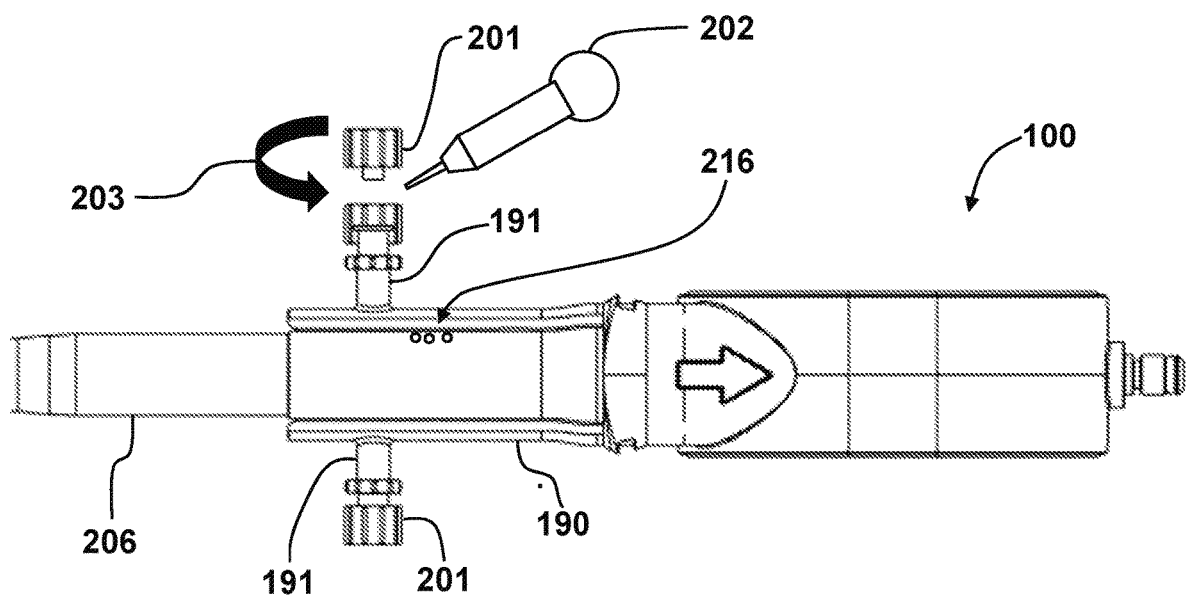

If air bubbles are nevertheless present within either one or more of the cannulas 206 (which can be made of a clear or translucent material) or the one or more purge devices 190 (which may also be made of a clear or translucent material) after inserting the one or more cannulas 206 into the one or more purge devices 190, the remaining bubbles can be purged using the one or more Luer ports 191, For example, as the cannula is inserted into the purge device 190 and before a cannula 206 engages the protruding cannula connector 141, a user can visually examine the clear/translucent cannula 206 and/or the clear/translucent purge device 190 to determine if there are any bubbles 216 remaining. See, for example, FIG. 15. If there are bubbles 216, the user can remove the cap 201 of one of the Luer ports 191 (typically the Luer port 191 nearest the bubbles 216), such as by twisting the cap in direction 203 and preferably with the Luer port 191 being oriented with the cap 201 positioned on top of (vertically above) the purge device 190. See, for example, FIG. 16, Once the cap 201 is removed a user can connect a syringe 202 to the Luer port 191, such as by engaging threads on syringe 202 with threads on the Luer port 191 and rotating the syringe 202 and the Luer port with respect to one another. In at least one embodiment it is preferable to have some air within the syringe 202, such as by the syringe 202 being half filled with a fluid, for example, a saline solution. The user can then squeeze the syringe 202 to fill the purge device 190 with additional fluid and release the syringe 202 to draw the bubbles out of the purge device 190 and into the syringe 202. This process can be repeated until all of the bubbles are purged from the purge device 190. Once all of the bubbles are removed from the purge device 190, the user may remove the syringe 202 from the Luer port 191 and replace the cap 201 onto the Luer port 191.

Figure 17:
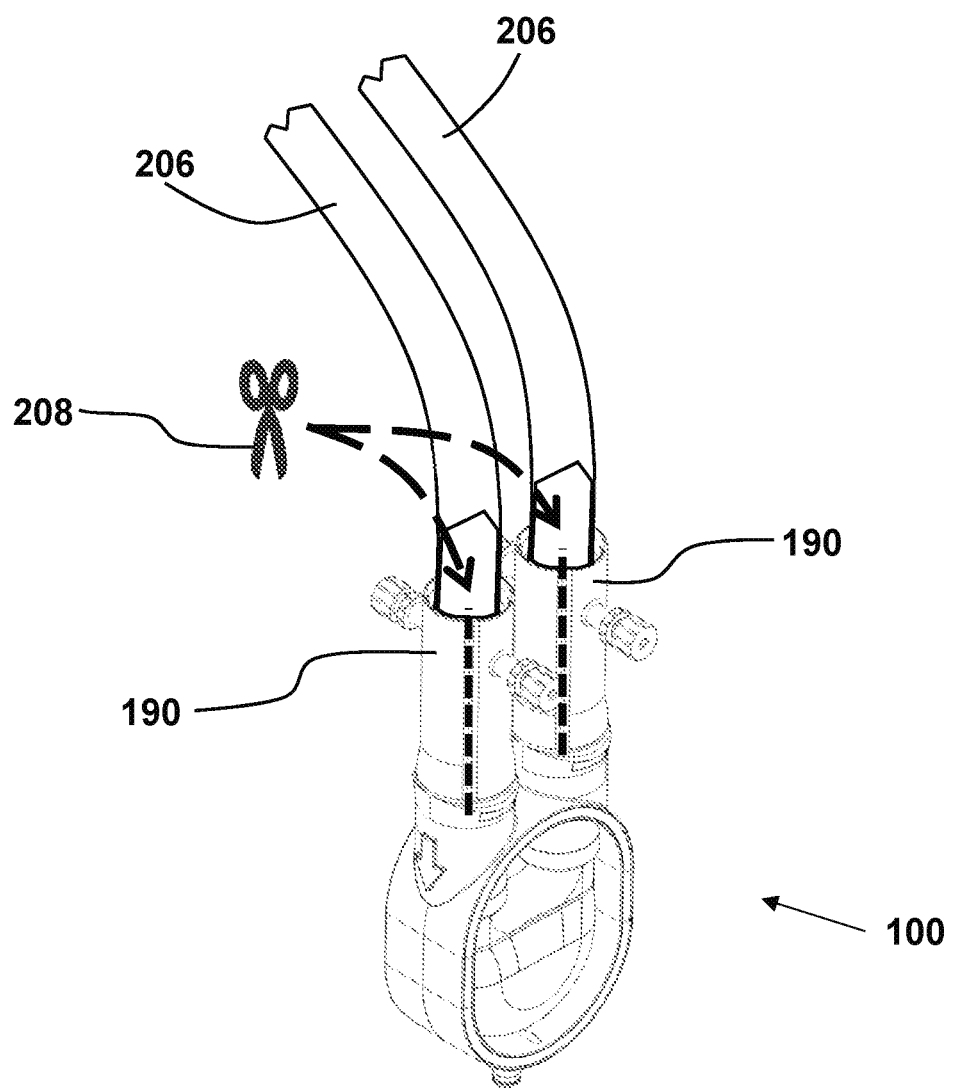
FIG. 17 depicts the removal of one or more purge devices from the ventricular assist device of FIG. 10 according to embodiments of the present disclosure.

Once the one or move cannulas 206 are attached to the ventricular assist device 100, a user may then remove the one or more purge devices 190 from the ventricular assist device 100. For example, in one example embodiment a user may cut the purge device 190 using a cutting device (for example, scissors 208). In one example, a user may cut the purge device 190 along the one or more grooves 194 as depicted in FIG. 17, and remove the purge device 190 from the ventricular assist device 100. Since the one or more cannulas 206 are attached to the ventricular assist device 100 prior to removal of the one or more purge devices 190, the likelihood of gas bubbles being introduced into the ventricular assist device 100 or the one or more cannulas 206 is eliminated.

After the one or more purge devices 190 are removed from the ventricular assist device 100, a user can install one or more cannula holders 170 to help hold the cannulas 206 to the cannula connector 140 as described above.

Various aspects of different embodiments of the present disclosure are expressed in paragraphs X1, X2, X3 and X4, as follows:

X1. One embodiment of the present disclosure includes a ventricular assist device for assisting in pumping blood to and from a heart that includes: a pump housing defining an interior chamber, a pump inlet, a pump outlet and an airflow channel, the airflow channel being pneumatically connected to the interior chamber; a cannula connector connected to the pump inlet or the pump outlet and configured to be inserted into a cannula; a sac disposed in the interior chamber and connected to the pump inlet and the pump outlet, the sac defining an interior volume; an airflow channel disposed through the pump housing and configured for flowing air into or out from the interior chamber, wherein air flowing into the interior chamber creates pressure on the sac to decrease the interior volume of the sac and air flowing out from the interior chamber decreases pressure on the sac to increase the interior volume of the sac; and a cannula holder including a first clasp and a second clasp, the first clasp configured to fasten the cannula to the connector and the second clasp configured to fasten the cannula holder to the connector.

X2. Another embodiment of the present disclosure includes a method for connecting a cannula to a ventricular assist device, the ventricular assist device defining a pump housing, a protruding cannula connector, and a cavity, the protruding cannula connector defining an axial blood flow direction, wherein the method includes: inserting the protruding cannula connector into the cannula; increasing the friction between the protruding cannula connector and the cannula by embracing the cannula with a first clasp; restraining the first clasp in the axial blood flow direction by inserting the second clasp into the cavity.

X3. Another embodiment of the present disclosure includes an apparatus that includes: a pump housing defining an interior chamber, a pump inlet, a pump outlet and an airflow channel, the airflow channel pneumatically connecting the interior chamber to the external environment; a sac disposed in the interior chamber and connected to the pump inlet and the pump outlet, the sac defining an interior volume; wherein air flowing into the interior chamber through the airflow channel creates pressure on the sac to decrease the interior volume of the sac and air flowing out from the interior chamber decreases pressure on the sac to increase the interior volume of the sac; means for connecting a cannula to the pump inlet or the pump outlet; and means for increasing friction between the cannula connector and the cannula.

X4. Yet another embodiment of the present disclosure includes a purge device for a ventricular assist device that includes: a purge device body defining an inner cavity, a first open end, and a second open end, wherein the first open end is configured and adapted to receive a cannula, wherein the inner cavity is configured to hold fluid, receive a cannula and guide the received cannula to the ventricular assist device to which the purge device is connected, wherein the second open end is configured and adapted to form a fluid tight seal with a ventricular assist device, wherein when the second open end is attached to a ventricular assist device, the cavity and the internal chamber of the ventricular assist device are in fluidic communication with one another, and wherein the purge device body is configured and adapted to be removed by hand after a cannula received within the cavity is connected to a ventricular assist device.

Yet other embodiments include the features described in any of the previous statements X1, X2. X3 or X4, as combined with (i) one or more of the previous statements X1, X2, X3 or X4, (ii) one or more of the following aspects, or (iii) one or more of the previous statements X1, X2, X3 or X4 and one or more of the following aspects described in the following paragraphs:

Wherein the first clasp of the cannula holder directly contacts the cannula when a cannula is fastened to the connector, and wherein the second clasp of the cannula holder directly contacts the connector when the cannula is fastened to the connector An inlet one-way valve for fitting in the pump inlet at an end of the inlet one-way valve and the sac at another end of the inlet one-way valve, the inlet one-way valve having three leaflets for opening and closing the pump inlet.

An outlet one-way valve for fitting in the pump outlet at an end of the outlet one-way valve and the sac at another end of the outlet one-way valve, the outlet one-way valve having three leaflets for opening and closing the pump outlet.

Wherein the pump housing connector comprises a connector body connected to the cannula connector and a cavity on the connector body.

Wherein the pump housing connector comprises a strip disposed between the cavity and the cannula connector, wherein the strip forms a ramp to help guide the second clasp into the cavity on the connector body.

Wherein a width at one point of the strip close to the cavity in a direction to which the cannula connector is extended is wider than a width at another point of the strip distant from the cavity.

Wherein the cannula connector defines a central axis, the second clasp extends in a direction substantially parallel to the cannula connector axis, and the second clasp is configured to be inserted into the cavity.

Wherein the first clasp is a non-closed shape configured to embrace a cannula, wherein a first end of the first clasp is configured to be fastened to a second end of the first clasp.

Wherein the first end of the first clasp is curved into a J-shaped structure and the second end of the first clasp is curved into a complimentary J-shape structure.

Wherein the cannula holder is a body of unitary construction.

Wherein the airflow channel bifurcates into two symmetrical conduits for distributing air homogeneously to a first space between a side of the pump housing and the sac and a second space between an opposite side to the side of the pump housing and the sac.

Wherein one of the two symmetrical conduits is connected to the first space and the other of the two symmetrical conduits is connected to the second space.

Wherein the pump housing comprises two housing halves that fit together.

At least one housing fastener for fastening the two housing halves together.

A torqueable wrench configured to rotate the housing fastener, the torqueable member including a sound generating member that makes a sound when a predetermined torque is applied to the housing fastener.

A purge device configured to be connected to the connector for removing bubbles from inside the sac.

Wherein the first and second clasps define a body of unitary construction.

Fastening a first end of the first clasp to a second end of the first clasp.

Connecting complimentary J-shaped features at a first end of the first clasp and a second end of the first clasp.

Wherein said means for connecting a cannula to the pump inlet includes a cannula connector configured for insertion into a cannula.

A cannula connector configured for insertion into a cannula.

Wherein said means for increasing friction between the cannula connector and the cannula includes a cannula holder configured to embrace the cannula.

A cannula holder configured to embrace the cannula.

Wherein said cannula holder includes means for axially latching the cannula holder to the pump housing.

Wherein the purge device body includes a membrane adjacent the first open end, the membrane defining an aperture configured and adapted to flexibly embrace and form a fluid tight seal with a cannula inserted through the membrane aperture.

Wherein the inner surface of the purge device defines one or more elongated guide members, wherein the one or more elongated guide members extend into the inner cavity and embrace a cannula inserted into the purge device.

Wherein the purge device is connected to a ventricular assist device.

Wherein the purge device includes one or more sealable openings configured and adapted to permit fluid to enter into the purge device and for bubbles to exit the purge device while the purge device is connected to a ventricular assist device and a cannula.

Wherein the purge device is configured to permit visual identification of bubbles within the purge device by a user.

Accordingly, the exemplary ventricular assist device 100 described above in detail can overcome the problems in the current state of the art in the ventricular assist device.

Reference systems that may be used herein can refer generally to various directions (e.g., upper, lower, forward and rearward), which are merely offered to assist the reader in understanding the various embodiments of the disclosure and are not to be interpreted as limiting. Other reference systems may be used to describe various embodiments, such as referring to the direction of projectile movement as it exits the firearm as being up, down, rearward or any other direction.

The term "and/or" indicates that items in a list can be taken together in various combinations or separately. For example, A, B and/or C can indicate A alone, B alone, C alone, A and B, A and C, or B and C.

While examples, one or more representative embodiments and specific forms of the disclosure have been illustrated and described in detail in the drawings and foregoing description, the same is to be considered as illustrative and not restrictive or limiting. The description of particular features in one embodiment does not imply that those particular features are necessarily limited to that one embodiment. Some or all of the features of one embodiment can be used or applied in combination with some or all of the features of other embodiments unless otherwise indicated, One or more exemplary embodiments have been shown and described. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

ELEMENT NUMBERING

Table 1 includes element numbers and at least one word used to describe the member and/or feature represented by the element number. It is understood that none of the embodiments disclosed herein are limited to these descriptions, other words may be used in the description or claims to describe a similar member and/or feature, and these element numbers can be described by other words that would be understood by a person of ordinary skill reading and reviewing this disclosure in its entirety.

TABLE 1

| | |
|---|---|
| 100 | Ventricular assist device |
| 101 | Blood flow |
| 102 | Fluid flow |
| 110 | Pump Housing |
| 111 | Pump inlet |
| 112 | Pump outlet |
| 113 | Upper housing halve |
| 114 | Lower housing halve |
| 115 | First space |
| 116 | Second space |
| 117 | Gasket |
| 118 | Inlet arrow |
| 119 | Outlet arrow |
| 120 | Housing fastener |
| 130 | One-way valve |
| 131 | Inlet valve |
| 132 | Outlet valve |
| 133 | Inlet three-leaflets |
| 134 | Outlet three-leaflets |
| 140 | Connector |
| 141 | Protruding cannula connector |
| 142 | Pump housing connector |
| 143 | Connector body |
| 144 | Cavity |
| 145 | Strip |
| 146 | Abutment surface |
| 147 | Edge |
| W1 | Width |
| W2 | Width |
| 150 | Sac |
| 160 | Pneumatic connector |
| 161 | Airflow channel |
| 162 | Pneumatic conduit |
| 163 | Connector |
| 170 | Cannula holder |
| 171 | First clasp |
| 172 | First end of first clasp |
| 173 | Second end of first clasp |
| 174 | Second clasp |
| 175 | First end of second clasp |
| 176 | Second end of second clasp |
| 177 | Open area |
| 178 | Protuberance |
| 179 | Open area |

TABLE 1-continued

| | |
|---|---|
| 130 | Torqueable wrench |
| 181 | Handle |
| 182 | Closure surface |
| 183 | Indicator arrow |
| 189 | Inner cavity |
| 190 | Purge device |
| 191 | Luer Port |
| 192 | Membrane |
| 193 | Guide channel |
| 194 | Groove |
| 195 | VAD engagement end |
| 196 | Open end |
| 197 | Ramp |
| 198 | Purge device body |
| 199 | Inner surface |
| 198 | Distance/diameter |
| 202 | Syringe |
| 204 | Forceps |
| 206 | Cannula |
| 207 | End of cannula |
| 208 | Scissors |
| 210 | Tap |
| 212 | Direction |
| 213 | Direction |
| 214 | Direction |
| 216 | Bubbles |

What is claimed is:

1. A ventricular assist device for assisting in pumping blood to and from a heart comprising:
   a pump housing defining an interior chamber, a pump inlet, a pump outlet and an airflow channel, the airflow channel being pneumatically connected to the interior chamber;
   a cannula connector connected to the pump inlet or the pump outlet and configured to be inserted into a cannula;
   a sac disposed in the interior chamber and connected to the pump inlet and the pump outlet, the sac defining an interior volume;
   an airflow channel disposed through the pump housing and configured for flowing air into or out from the interior chamber, wherein air flowing into the interior chamber creates pressure on the sac to decrease the interior volume of the sac and air flowing out from the interior chamber decreases pressure on the sac to increase the interior volume of the sac; and
   a cannula holder including a first clasp and a second clasp, the first clasp configured to fasten the cannula to the cannula connector and the second clasp configured to fasten the cannula holder to the cannula connector.

2. The ventricular assist device of claim 1, wherein the first clasp of the cannula holder directly contacts the cannula when a cannula is fastened to the cannula connector, and wherein the second clasp of the cannula holder directly contacts the cannula connector when the cannula is fastened to the cannula connector.

3. The ventricular assist device of claim 1, further comprising:
   an inlet one-way valve for fitting in the pump inlet at an end of the inlet one-way valve and the sac at another end of the inlet one-way valve, the inlet one-way valve having three leaflets for opening and closing the pump inlet; and
   an outlet one-way valve for fitting in the pump outlet at an end of the outlet one-way valve and the sac at another end of the outlet one-way valve, the outlet one-way valve having three leaflets for opening and closing the pump outlet.

4. The ventricular assist device of claim 1, further comprising:
   a pump housing connector, wherein the pump housing connector comprises a connector body connected to the cannula connector and a cavity on the connector body.

5. The ventricular assist device of claim 4, the pump housing connector comprises a strip disposed between the cavity and the cannula connector, wherein the strip forms a ramp to help guide the second clasp into the cavity on the connector body.

6. The ventricular assist device of claim 4, wherein a width at one point of the strip close to the cavity in a direction to which the cannula connector is extended is wider than a width at another point of the strip distant from the cavity.

7. The ventricular assist device of claim 4, wherein the cannula connector defines a central axis, the second clasp extends in a direction substantially parallel to the cannula connector axis, and the second clasp is configured to be inserted into the cavity.

8. The ventricular assist device of claim 1, wherein the first clasp is a non-closed shape configured to embrace a cannula, wherein a first end of the first clasp is configured to be fastened to a second end of the first clasp.

9. The ventricular assist device of claim 8, wherein the first end of the first clasp is curved into a J-shaped structure and the second end of the first clasp is curved into a complimentary J-shape structure.

10. The ventricular assist device of claim 1, wherein the cannula holder is a body of unitary construction.

11. The ventricular assist device of claim 1, wherein the airflow channel bifurcates into two symmetrical conduits for distributing air homogeneously to a first space between a side of the pump housing and the sac and a second space between an opposite side to the side of the pump housing and the sac, wherein one of the two symmetrical conduits is connected to the first space and the other of the two symmetrical conduits is connected to the second space.

12. The ventricular assist device of claim 1, wherein the pump housing comprises two housing halves that fit together, the ventricular assist device comprising:
   at least one housing fastener for fastening the two housing halves together.

13. The ventricular assist device of claim 12, further comprising:
   a torqueable wrench configured to rotate the housing fastener, the torqueable member including a sound generating member that makes a sound when a predetermined torque is applied to the housing fastener.

14. The ventricular assist device of claim 1, further comprising:
   a purge device configured to be connected to the cannula connector for removing bubbles from inside the sac.

* * * * *